United States Patent [19]
Ebel et al.

[11] Patent Number: 5,640,464
[45] Date of Patent: Jun. 17, 1997

[54] METHOD AND SYSTEM FOR INSPECTING PACKAGES

[75] Inventors: James Ebel; Michael Francis Widman, both of Jacksonville, Fla.; Peter W. Sites; Peyman H. Dehkordi, both of Knoxville, Tenn.

[73] Assignee: Johnson & Johnson Vision Products, Inc., Jacksonville, Fla.

[21] Appl. No.: 251,525

[22] Filed: May 31, 1994

[51] Int. Cl.$^6$ ............................................. G06K 9/62
[52] U.S. Cl. ................................. 382/143; 382/224
[58] Field of Search ................................. 382/143, 141, 382/203, 224, 225, 286, 159; 348/127, 86; 356/239, 240

[56] References Cited

U.S. PATENT DOCUMENTS

| | | | |
|---|---|---|---|
| 3,932,042 | 1/1976 | Faani et al. | 348/127 |
| 3,942,900 | 3/1976 | Garris | 356/237 |
| 3,969,227 | 7/1976 | Garris | 209/73 |
| 4,399,367 | 8/1983 | Grube et al. | 250/560 |
| 4,549,205 | 10/1985 | Misaki et al. | 358/106 |
| 4,771,469 | 9/1988 | Wittenburg | 382/25 |
| 5,080,839 | 1/1992 | Kindt-Larsen | 264/2.6 |
| 5,099,987 | 3/1992 | Bieri | 206/5.1 |
| 5,229,837 | 7/1993 | Osakada | 356/240 |

FOREIGN PATENT DOCUMENTS

| | | | |
|---|---|---|---|
| 35 32 068 A1 | 4/1986 | Germany | G01N 21/90 |
| 41 36 025 A1 | 5/1992 | Germany | G01N 21/84 |
| 2 133 873 | 8/1984 | United Kingdom | G01N 21/90 |

Primary Examiner—Michael T. Razavi
Assistant Examiner—Jon Chang

[57] ABSTRACT

A method and system for verifying the presence of a lens in a transparent package. The method comprises the steps of moving the package into an inspection position, and conducting a light beam through the package and onto an image plane to form an image of the package on the image plane. The method further comprises the steps of generating a set of signals representing the image on the image plane, and analyzing those signals to determine whether a lens is present in the package. This analyzing step, in turn, includes the steps of searching the package image for images of discrete objects; and for each object image found in the package image, identifying values for a plurality of parameters, and analyzing those identified values according to a predetermined procedure to identify the object as a lens or as not a lens. A lens present signal is generated if one object image found in the package image is identified as a lens; and a lens missing signal is generated if no object images are found in the package image, or if all object images found in the package image are identified as not lenses.

8 Claims, 18 Drawing Sheets

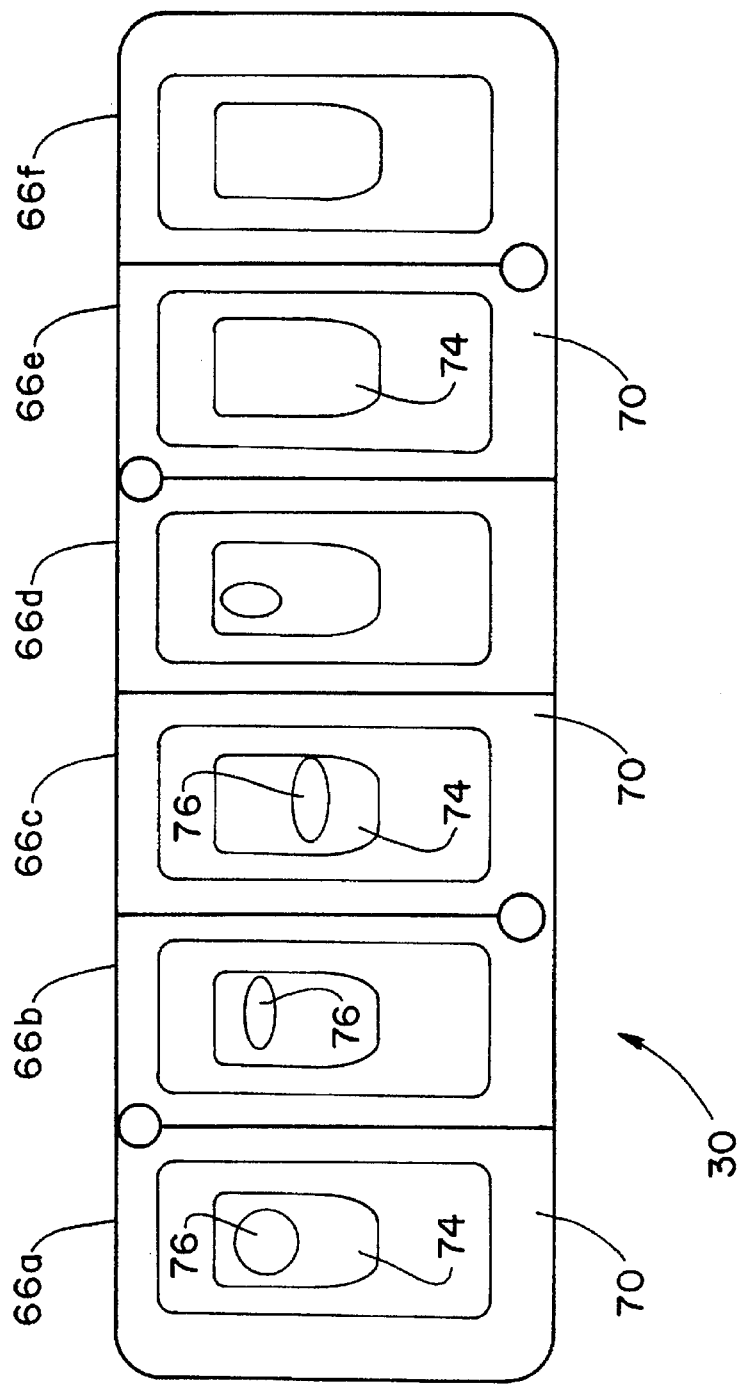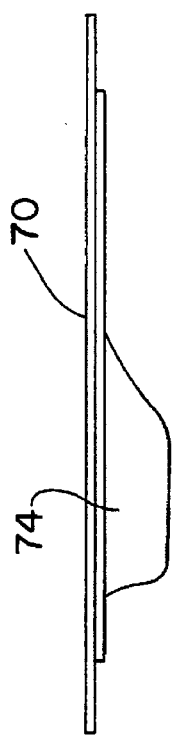

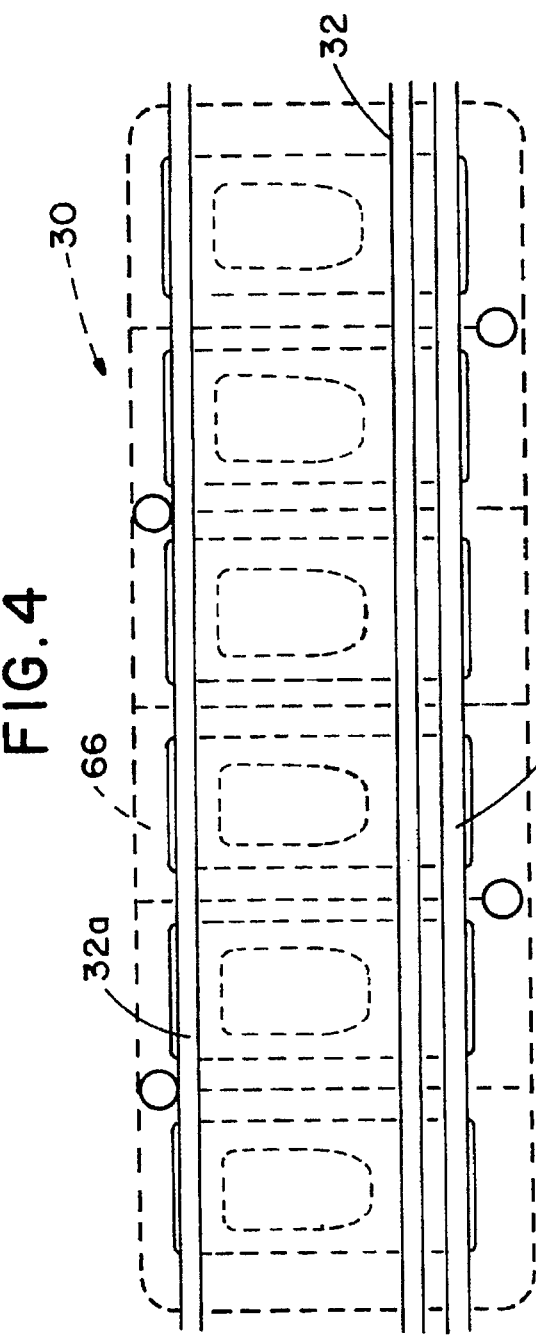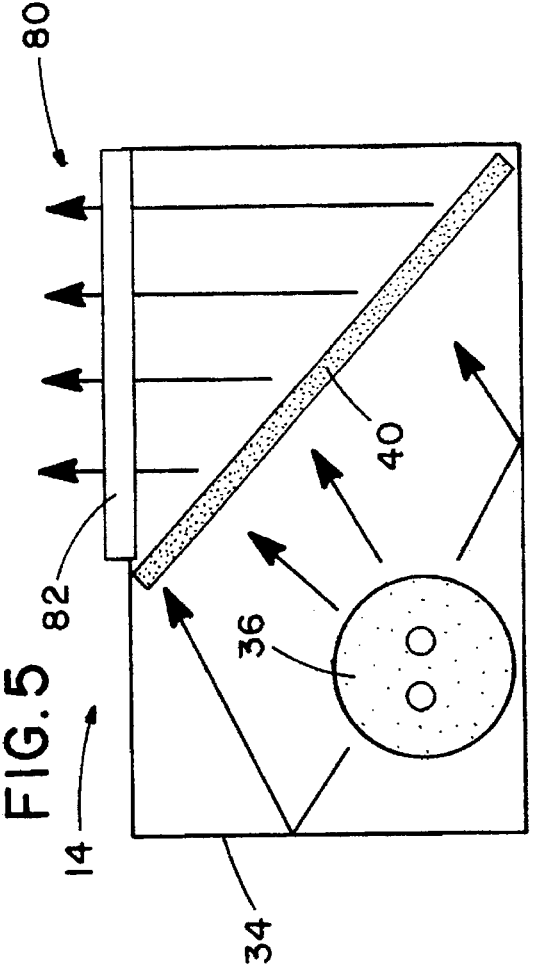

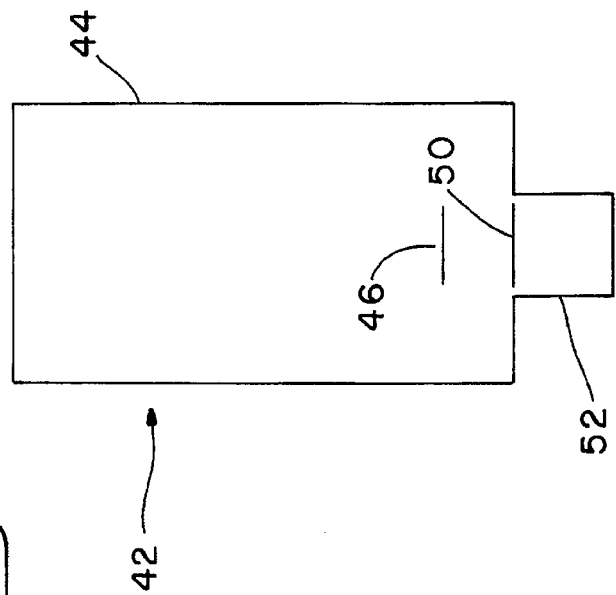
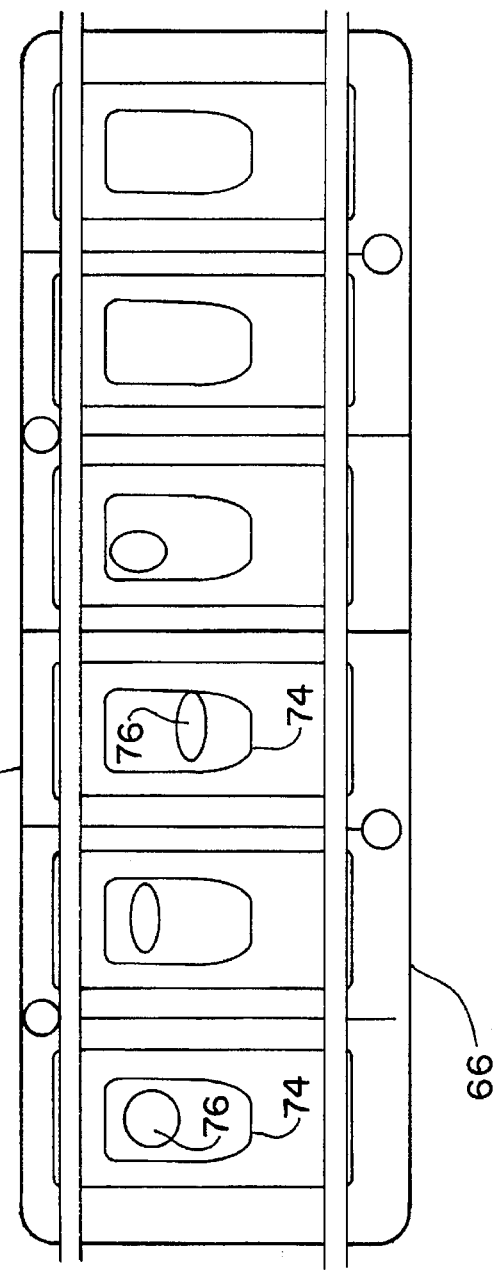

FIG. 15

| $P_{i-1,j-1}$ | $P_{i-1,j}$ | $P_{i-1,j+1}$ |
|---|---|---|
| $P_{i,j-1}$ | $P_{i,j}$ | $P_{i,j+1}$ |
| $P_{i+1,j-1}$ | $P_{i+1,j}$ | $P_{i+1,j+1}$ |

Strong Edge All Over — Unfolded Lens

Strong Edge All Over — Folded Lens

Strong Edge Partially — Weak Edge

Strong Edge Partially — Weak Edge

FIG. 22A

| | | | | |
|---|---|---|---|---|
| 2960 | 14.90 | 1.85 | 210 | 1 |
| 2960 | 105.95 | 1.85 | 560 | 1 |
| 2924 | 79.78 | 1.58 | 483 | 1 |
| 2886 | 53.24 | 1.90 | 392 | 1 |
| 2886 | 15.14 | 1.90 | 209 | 1 |
| 2886 | 118.99 | 1.90 | 586 | 1 |
| 2886 | 50.83 | 1.90 | 383 | 1 |
| 2880 | 14.88 | 1.80 | 207 | 1 |
| 2856 | 19.67 | 1.62 | 237 | 1 |
| 2852 | 33.48 | 1.35 | 309 | 1 |
| 2847 | 23.20 | 1.87 | 257 | 1 |
| 2812 | 33.52 | 1.95 | 307 | 1 |
| 2812 | 15.09 | 1.95 | 206 | 1 |
| 2812 | 44.82 | 1.95 | 355 | 1 |
| 2812 | 42.82 | 1.95 | 347 | 1 |
| 2812 | 13.66 | 1.95 | 196 | 1 |
| 2812 | 54.09 | 1.95 | 390 | 1 |
| 2795 | 29.47 | 1.51 | 287 | 1 |
| 2730 | 64.00 | 1.79 | 418 | 1 |
| 2680 | 77.93 | 1.68 | 457 | 1 |
| 2664 | 21.08 | 2.06 | 237 | 1 |
| 2664 | 36.31 | 2.06 | 311 | 1 |
| 2604 | 73.00 | 1.48 | 436 | 1 |
| 2516 | 14.80 | 2.18 | 193 | 1 |
| 2484 | 16.59 | 2.00 | 203 | 1 |
| 2482 | 43.61 | 2.15 | 329 | 1 |
| 2479 | 17.12 | 1.81 | 206 | 1 |
| 2479 | 15.03 | 1.81 | 193 | 1 |
| 2475 | 80.82 | 1.36 | 471 | 1 |
| 2376 | 82.60 | 2.18 | 443 | 1 |
| 2310 | 18.19 | 1.89 | 205 | 1 |
| 2301 | 17.21 | 1.51 | 199 | 1 |
| 2240 | 113.40 | 2.19 | 504 | 1 |
| 2208 | 13.71 | 2.16 | 174 | 1 |
| 1984 | 38.67 | 2.06 | 277 | 1 |
| 3330 | 102.42 | 1.64 | 584 | F |
| 3108 | 14.73 | 1.76 | 214 | F |
| 2948 | 137.64 | 1.52 | 637 | F |
| 2850 | 53.64 | 1.14 | 391 | F |
| 2814 | 37.07 | 1.6 | 323 | F |
| 2774 | 57.1 | 1.92 | 398 | F |
| 2760 | 70.78 | 1.73 | 442 | F |
| 2698 | 15.88 | 1.87 | 207 | F |
| 2666 | 21.79 | 1.44 | 241 | F |
| 2664 | 18 | 2.06 | 219 | F |
| 2652 | 18.25 | 1.74 | 220 | F |
| 2590 | 56.93 | 2.11 | 384 | F |
| 2576 | 12.58 | 1.22 | 180 | F |
| 2556 | 109.9 | 3.97 | 530 | F |
| 2542 | 18.52 | 1.51 | 217 | F |
| 2494 | 124.85 | 1.35 | 558 | F |
| 2442 | 30.52 | 2.24 | 273 | F |
| 2419 | 26.46 | 1.44 | 253 | F |
| 2394 | 14.14 | 1.66 | 184 | F |
| 2368 | 65.89 | 2.31 | 395 | F |

FIG. 22B

| | | | | |
|---:|---:|---:|---:|---|
| 2320 | 13.97 | 1.45 | 180 | F |
| 2244 | 25.88 | 2.06 | 241 | F |
| 2214 | 31.72 | 1.32 | 265 | F |
| 1702 | 32.45 | 3.22 | 235 | F |
| 1600 | 15.02 | 1.56 | 155 | F |
| 1344 | 69.67 | 3.05 | 306 | F |
| 1160 | 24.04 | 1.38 | 167 | F |
| 1155 | 16.49 | 1.06 | 138 | F |
| 1050 | 42.4 | 2.38 | 211 | F |
| 980 | 34.92 | 1.25 | 185 | F |
| 3050 | 124.01 | 1.22 | 615 | OS |
| 2835 | 23.84 | 1.4 | 260 | OS |
| 2590 | 44.37 | 2.11 | 339 | OS |
| 2280 | 33.65 | 1.43 | 277 | OS |
| 2244 | 82.4 | 1.94 | 430 | OS |
| 2064 | 52.44 | 1.12 | 329 | OS |
| 1998 | 95.58 | 1.73 | 135 | OS |
| 1988 | 117.84 | 2.54 | 484 | OS |
| 1652 | 36.93 | 2.11 | 247 | OS |
| 705 | 31.07 | 3.13 | 148 | OS |
| 3480 | 36.78 | 1.55 | 302 | P |
| 3478 | 71.88 | 1.57 | 500 | P |
| 3330 | 77.80 | 1.56 | 138 | P |
| 3312 | 82.27 | 1.57 | 522 | P |
| 3256 | 221.30 | 1.68 | 850 | P |
| 3234 | 56.91 | 1.35 | 429 | P |
| 3108 | 27.06 | 1.76 | 290 | P |
| 3066 | 40.87 | 1.74 | 354 | P |
| 3015 | 69.27 | 1.49 | 457 | P |
| 2982 | 69.73 | 1.69 | 456 | P |
| 2960 | 70.56 | 1.85 | 457 | P |
| 2870 | 56.59 | 1.71 | 403 | P |
| 2812 | 105.24 | 1.95 | 544 | P |
| 2769 | 42.49 | 1.82 | 343 | P |
| 2747 | 52.29 | 1.63 | 379 | P |
| 2745 | 46.95 | 1.36 | 359 | P |
| 2720 | 17.79 | 1.7 | 220 | P |
| 2701 | 66.25 | 1.97 | 423 | P |
| 2664 | 44.16 | 1.95 | 343 | P |
| 2623 | 26.37 | 1.42 | 263 | P |
| 2590 | 100.42 | 2.11 | 510 | P |
| 2584 | 72.22 | 1.79 | 432 | P |
| 2574 | 16.17 | 1.69 | 204 | P |
| 2535 | 57.87 | 1.67 | 383 | P |
| 2380 | 100.88 | 2.06 | 490 | P |
| 2356 | 48.78 | 1.63 | 339 | P |
| 2295 | 27.67 | 1.13 | 252 | P |
| 2268 | 41.56 | 1.29 | 307 | P |
| 2112 | 18.38 | 1.94 | 197 | P |
| 1849 | 61.42 | 1 | 337 | P |
| 1824 | 27.02 | 1.78 | 222 | P |
| 1782 | 40.31 | 2.44 | 268 | P |
| 903 | 25.25 | 2.05 | 151 | P |
| 782 | 16.91 | 1.48 | 115 | P |
| 308 | 19.75 | 1.75 | 78 | W |

METHOD AND SYSTEM FOR INSPECTING PACKAGES

BACKGROUND OF THE INVENTION

This invention generally relates to automated methods and systems for inspecting packages; and more specifically, to automated methods and systems to verify the presence of lenses in packages.

Recently, several automated systems have been developed for producing ophthalmic lenses, particularly contact lenses; and for example, one such system is disclosed in U.S. Pat. No. 5,080,839. These systems have achieved a very high degree of automation; and, for instance, the lenses may be molded, removed from the molds, further processed and packaged all without any direct human involvement. Even with these highly automated systems, however, normally after the lenses are packaged, each package is inspected by a person to verify that the package contains a lens.

This personal inspection of the lens packages represents a significant cost, and it is believed that the cost of the package inspection can be substantially reduced if the inspection is done by automated means. In addition, although these personal inspections are highly accurate, it is believed that the reliability of the package inspections could be made even more accurate by employing appropriate automated inspection means to verify the presence of lenses in the packages.

SUMMARY OF THE INVENTION

An object of this invention is to provide an automated system and method for inspecting packages to verify that lenses are in the packages.

Another object of the present invention is to inspect lens packages automatically at a rate of about 12 packages a minute to verify that lenses are in the packages and with an error rate of less than about 1%.

A further object of this invention is to provide an automated system for inspecting lens packages to verify that lenses are in those packages with a false-negative error rate of less than about 1.0%.

These and other objectives are attained with a method and system for verifying the presence of a lens in a transparent package. The method comprises the steps of moving the package into an inspection position, and conducting a light beam through the package and onto an image plane to form an image of the package on the image plane. The method further comprises the steps of generating a set of signals representing the image on the image plane, and analyzing those signals to determine whether a lens is present in the package. This analyzing step, in turn, includes the steps of searching the package image for images of discrete objects; and for each object image found in the package image, identifying values for a plurality of parameters, and analyzing those identified values according to a predetermined procedure to identify the object as a lens or as not a lens. A lens present signal is generated if one object image found in the package image is identified as a lens; and a lens missing signal is generated if no object images are found in the package image, or if all object images found in the package image are identified as not lenses.

Further benefits and advantages of the invention will become apparent from a consideration of the following detailed description given with reference to the accompanying drawings, which specify and show preferred embodiments of the invention.

BRIEF DESCRIPTION OF THE DRAWINGS

FIG. 2 shows a group of packages that may be inspected in the system of FIG. 1.

FIG. 3 is a side view of one of the packages shown in FIG. 2.

FIG. 4 illustrates a portion of a transport subsystem that may be used in the system of FIG. 1.

FIG. 5 is a block diagram of an illumination subsystem that may be used in the inspection system of FIG. 1.

FIG. 6 shows an image that may be produced by the illumination subsystem of FIG. 5.

FIG. 7 illustrates one of the cameras of the system of FIG. 1.

FIG. 15 illustrates a preferred notation for identifying pixels.

FIG. 22 is a table showing data samples that were used to determine a classifier for use in the operation of this invention.

DETAILED DESCRIPTION OF THE PREFERRED EMBODIMENTS

Figure 1:
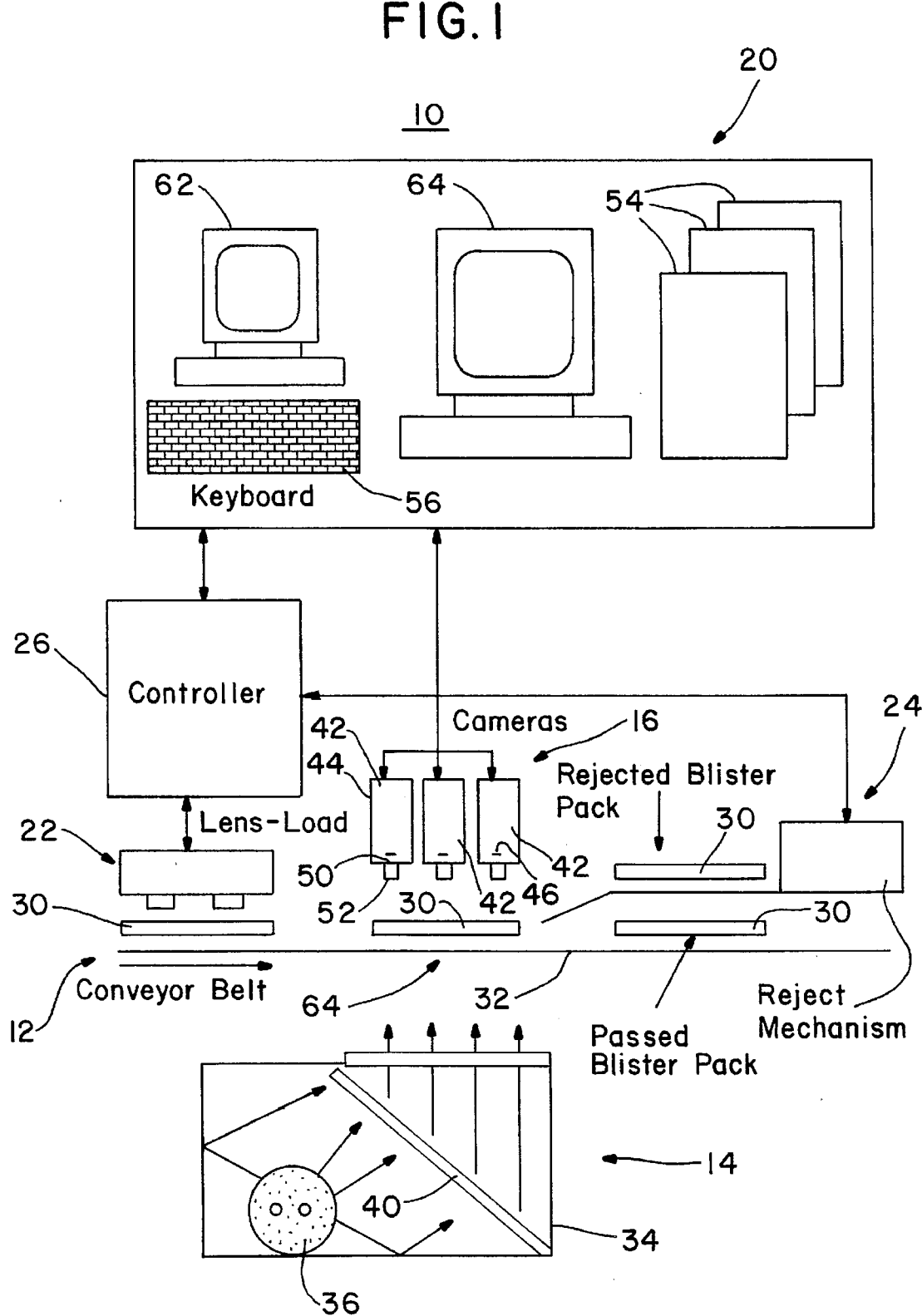
FIG. 1 is a block diagram illustrating a package inspection system embodying the present invention.

FIG. 1 is a block diagram illustrating package inspection system 10; and generally, system 10 comprises transport subsystem 12, illumination subsystem 14, imaging subsystem 16, and image processing subsystem 20. FIG. 1 also shows lens loading mechanism or assembly 22, reject mechanism or assembly 24, controller 26, and a plurality of groups of lens packages 30 referred to as blisterpacks.

With the preferred embodiment of system 10, transport subsystem 12 includes conveyor belt 32; and illumination subsystem 14 includes housing 34, light source 36, and diffuser 40. Also, with this preferred system 10, imaging subsystem 16 includes a plurality of cameras 42; and each of these cameras includes housing 44, pixel array 46, shutter 50, and lens assembly 52. As shown in FIG. 1, image processing subsystem 20 includes a plurality of processing and memory boards 54, input means such as keyboard 56, and preferably subsystem 20 further includes video monitor 60 and keyboard terminal 62.

Generally, transport subsystem 12 is provided to move a multitude of lens packages along a predetermined path and into a package inspection position, referenced at 64 in FIG. 1. Illumination subsystem 14 is provided to generate a light beam and to direct that beam through the lens packages moving through the package inspection system. Subsystem 16 generates a set of signals representing the light beam transmitted through each inspected lens package, and then transmits those signals to processing subsystem 20. The image processing subsystem receives those signals from subsystem 16 and processes these signals according to a predetermined program; and for each inspected lens package, subsystem 20 generates either a lens present signal or a lens missing signal indicating, respectively, that a lens is present or missing in the package.

Subsystem 10 may be used to inspect a large variety of types and sizes of packages, and FIG. 2 shows a group of packages 66a–66f that may be inspected in system 10. The packages 66 shown in FIG. 2 are connected together to form a blisterpack 30. With reference to FIGS. 2 and 3, each package includes a shell 70 that forms a cavity or recess 74. The shell 70 may be formed from a transparent plastic material, and preferably the shell is sufficiently rigid to maintain its shape under normal use. In addition, preferably, when a package 66 is inspected, the cavity 72 of the package is not covered.

With the group of packages 66a–66f shown in FIG. 2, lenses 76 are disposed in the cavities of packages 66a–66d, however lenses are missing from packages 66e and 66f. Also, the lenses 76 in packages 66a–66f are shown in various orientations. For instance, FIG. 2 shows a plan view of the lens in package 66a, the lenses in packages 66b and 66c are tilted about axes extending from left to right as viewed in FIG. 2, and the lens in package 66d is tilted slightly about an axis extending from top to bottom in FIG. 2.

System 10 may be used independent of any specific method or apparatus for placing or depositing lenses 76 in packages 66. System 10 is well suited, though, for use in a larger system in which lenses 76 are automatically made, inspected, treated, and then placed in packages 66 by robots at the lens loading mechanism 22.

With reference to FIGS. 1 and 4, transport subsystem 12 includes a conveyor belt 32 and a pair of parallel rails 32a and 32b. Belt 32 is mounted on a pair, or more, of pulleys (not shown) that support the belt for movement around an endless path, and one of those pulleys may be connected to a suitable drive means (not shown) to rotate the pulley and, thereby, move the conveyor belt around that endless path. Preferably, the drive means is operated so that packages 66 are moved or indexed through system 10 in a discontinuous or stepwise manner, and in particular, each package is stopped for a brief period of time below lens loading mechanism 22 and below imaging subsystem 16.

When the packages 66 are held below lens loading mechanism 22, that mechanism is used to deposit a lens 76 in the cavity 74 of each package. Various lens loading mechanisms are known in the art, and any suitable lens loading mechanism may be used with the present invention. Commonly, these lens loading mechanisms include a robot or a robot arm, sometimes referred to as a robot cell, that is used to carry lenses 76 from a supply or source thereof and to deposit those lenses in the cavities 74 of packages 66. With the preferred embodiment of the invention, in which packages 66 are connected together to form a blisterpack, lens loading mechanism 22 deposits three lenses at a time in each blisterpack. After lenses 76 have been deposited in all six cavities 74 of a blisterpack 32, that pack is indexed, or moved, forward into the inspection position 64. Transport subsystem 12 is described in greater detail in copending application no. filed herewith for "Automated Inspection System with Transport and Ejector Conveyor" (attorney docket 9305), the disclosure of which is herein incorporated by reference.

In addition, any suitable reject mechanism 24 may be used in system 10. Preferably, mechanism 24 is controlled by controller 26. More particularly, when controller 26 receives a signal from subsystem 20 that a specific blisterpack is missing a lens, controller 26 actuates mechanism 26 to remove that blisterpack from the stream of blisterpacks moving past the reject mechanism. Ejector mechanism 24 is also described in greater detail in the above identified copending application no. filed herewith for ("Automated Inspection System with Transport and Ejector Conveyor."

With reference to FIGS. 1 and 5, subsystem 14 is used to generate a light beam 80 and to direct that beam through the packages 66 in the inspection position 64. More specifically, light source 36, which may be a fluorescent light tube, is disposed in housing 34 and generates light beam 80. That beam 80 is reflected off the interior walls of housing 34, passes through diffuser 40 and exits housing 34 via a window 82, which may be, for example, a clear lexan cover plate.

It has been found that a specific wavelength of illumination is not necessary in the practice of the present invention. This is because the grey level gradient formed by the lens edges in the packages 66 is sufficient to detect the lens. Thus, the illumination for system 10 may be supplied by a regular fluorescent light tube.

Most fluorescent lighting is non uniform, however, and preferably subsystem 14 produces a light beam having a uniform irradiance. To overcome the irradiance irregularities within fluorescent tube 36 and to present to the blisterpack 30 a wider apparent illuminated field, diffuser 40 is installed above the fluorescent tube. Diffuser 40, which may be made of flashed opal, helps to produce in a relatively short distance, a light beam with the desired uniform irradiance, allowing subsystem 14 to be located comparatively close to conveyor belt 32.

As FIG. 5 particularly illustrates, bulb 36 can be offset from the axis formed by light beam 80 as that beam exits housing 34, and diffuser plate 40 can be placed at an angle not orthogonal to that light beam axis. The Lambertian scattering character of plate 40 then directs the radiant energy from the bulb upward uniformly in the transverse lateral direction. Lambert's Law states that if the luminous intensity perpendicular to a uniformly diffusing surface S is denoted by $I_o$, then the intensity $I_a$ at an angle normal to that surface is given by $I_o \cos(a)$. This is due to the apparent size difference in the surface section S when viewed at an angle not orthogonal to the surface. Thus, for a=45°, $I_a=(0.71)I_o$.

As shown in FIG. 5, plate 40 is placed at a 45 degree angle, which according to Lambert's Law, diminishes the maximum luminous intensity by less than thirty percent, and distributes the energy uniformly to within ten percent variability. In practice, the flashed opal absorbs slightly more than thirty percent since it is only an approximation to the perfect Lambertian surface. The arrangement of the diffuser 40 between the bulb 36 and blisterpack 30 also serves to increase the effective optical path between the bulb and the blisterpack. Ground glass has long been used in optics to simulate distant sources, at finite conjugates, and the flashed opal has an even greater angular effect. Because the bulb 36 is no longer directly beneath the blisterpack 30, only the uniformly scattered light proceeds upward. Preferably, the longitudinal axis of fluorescent bulb 36 is parallel to the longitudinal axis of the blisterpacks as those blisterpacks pass above illumination subsystem 14, and the bulb 36 is longer than the blisterpacks, an arrangement that helps to produce a more uniform illumination of each blisterpack.

Light fluctuations from image to image are preferably eliminated. The flicker caused by the normal 60 Hz ballast frequency, 0.0166 seconds per cycle, can be picked up by the camera focal plane array when operating at shutter speeds greater than 0.001 seconds. A high frequency ballast from Mercron eliminates this flicker, as it oscillates voltage at 60,000 Hz, or 0.000016 seconds per cycle. During the 0.001 second cycle of the electronic shutter, the lamp 36 experiences 60 full cycles in voltage, and the decay rate of the lamp phosphor keeps the illumination constant. This solution assumes that the voltage source for the ballast is constant.

The illumination subsystem 14 shown in the drawings produces images of packages 66 in which the lenses 76 can be distinguished from the rest of the packages; and for example, FIG. 6 shows an image of a blisterpack 30 that may be produced by light beam 80. Most of the light transmitted through each package is not attenuated, or is attenuated only very slightly, by the package. The edges of packages 66 and cavities 74 deflect light, producing corresponding dark lines on the image of the blisterpack. The edges of lenses 76 also deflect light passing through those edges, likewise forming corresponding dark areas on the image. The portions of light beam 80 passing through the lenses 76 themselves are slightly attenuated by the lenses, and as a result, the images of the lenses are not as bright as the images of the non-edge portions of the lens packages.

Figure 8:
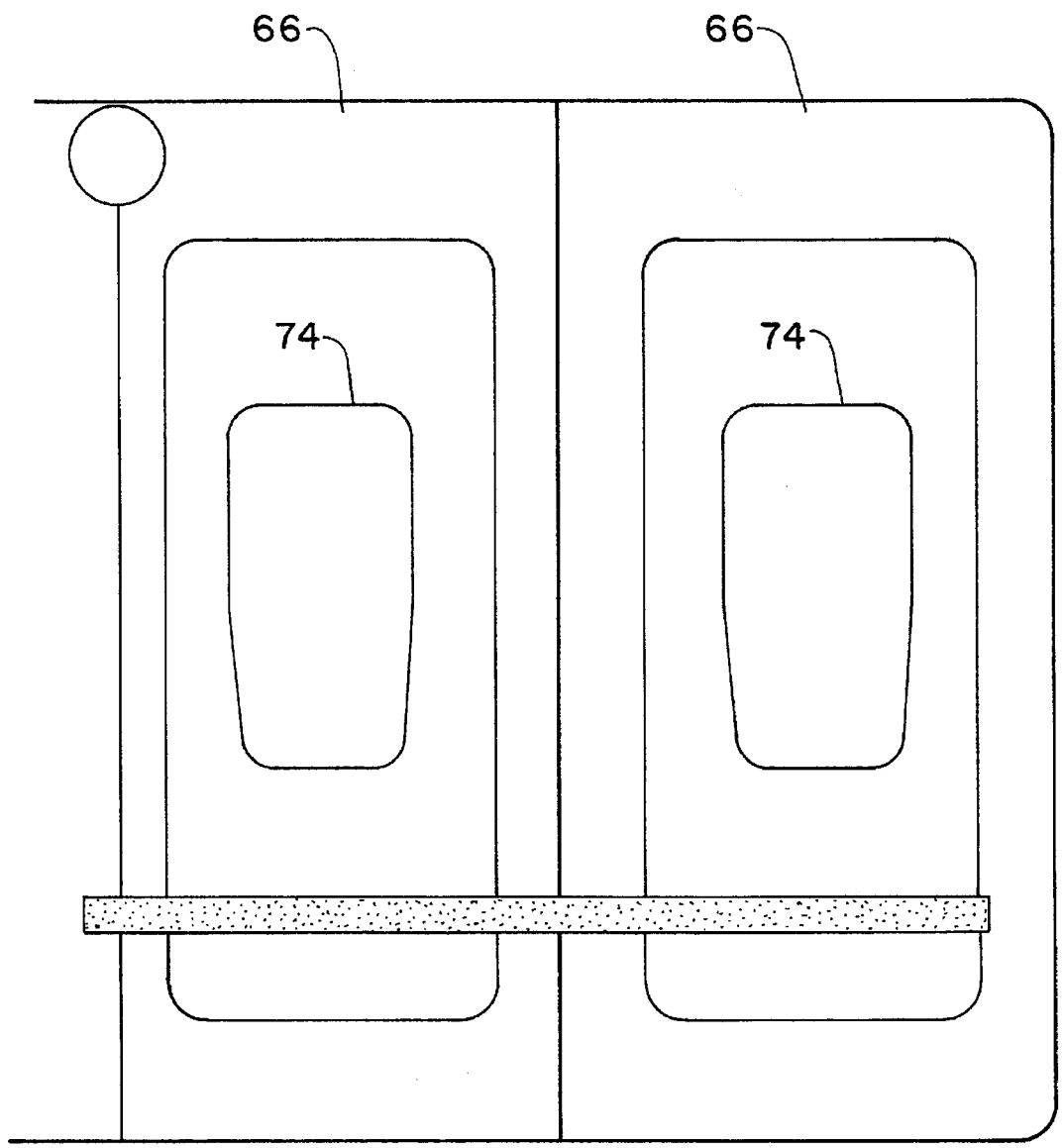
FIG. 8 illustrates a typical image that may be received by one of the cameras of the system shown in FIG. 1.

Imaging subsystem 16 receives the light beam transmitted through the lens package or packages 66 in the inspection position 64, and generates a series of signals representing that light beam. As previously mentioned, the embodiment of subsystem 16 shown in the drawings includes three cameras 42, which preferably are identical. With reference to FIG. 7, in each camera 42, pixel array 46 is disposed inside camera housing 44, directly behind shutter 50. Also, each pixel array is preferably comprised of a multitude of light sensors, each of which is capable of generating a respective one electric current having a magnitude proportional to or representing the intensity of light incident on that sensor. Further, in the preferred operation of system 10, when a given blisterpack is inspected, each of the three cameras 42 receives the images of a respective pair of the six packages 66 in the blisterpack; and FIG. 8 illustrates a typical image that may be received by one of the cameras, specifically the pixel array thereof.

As is conventional, preferably the light sensors, or pixels, of each pixel array 46 are arranged in a uniform grid of a given number of rows and columns, and for example, that grid may consist of one million pixels arranged in approximately one thousand columns and one thousand rows. Preferably, in that grid, the rows and columns of the grid are both uniformly spaced apart; and except for those pixels along the very edge of the array, each pixel has eight immediate neighbors.

As will be understood by those of ordinary skill in the art, any suitable camera or cameras may be used in subsystem 16. For instance, each camera 42 may be a Panasonic GP-MF552 black and white CCD camera. The camera outputs images in RS-170 mode, with 2-line interlace. Only one of the line interlace frames is grabbed by the image processor input in order to limit the image size to under 200,000 pixels. Keeping the total image size under this threshold is helpful in sizing the required memory for the processor boards 54, and thereby limiting the cost of the inspection and processing system.

A 16 mm C-mount lens from Computar attaches to the CCD camera, and a Tiffen sky filter protects the lens and diminishes glare. The lighting subsystem 14 does not need to freeze the motion of the lens movement underneath the camera 42, because the transport belt 32 is indexed instead of continuously moving. Also, the 0.001 second exposure afforded by the electronic shutter feature of the camera 42 creates an adequately sharp image, and vibrations from neighboring robotics and motors do not affect the image quality.

Processing subsystem 20 receives the signals from imaging subsystem 16, specifically pixel arrays 46, and processes those signals, according to a predetermined program discussed below in detail, to classify each package 66 as either having or not having a lens. More specifically, the electric signals from the pixel array 46 of each camera 42 are conducted to processor board 54. The processor board converts each electric current signal from each pixel of each array 46 into a respective digital data value, and stores that data value at a memory location having an address associated with the address of the pixel that generated the electric signal.

Figure 9:
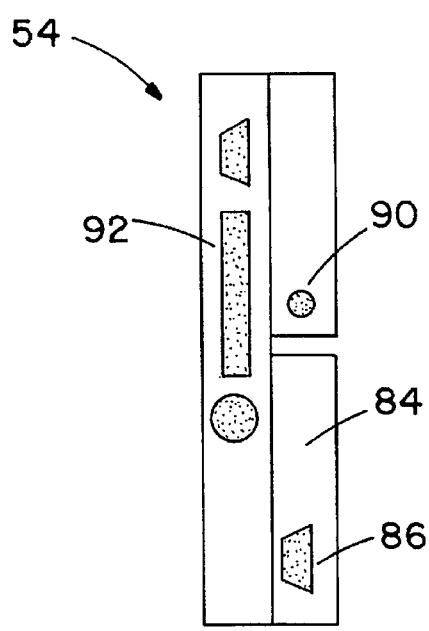
FIG. 9 shows a processing board of a processing subsystem that may be used in the inspection system of FIG. 1.

Any appropriate processing unit 54 may be employed in system 10; and, for instance, the processing unit may be an IP940 Image Processor Machine Vision Board sold by Perceptics Corp. With reference to FIG. 9, this processing board has three camera inputs on a monodigitizer board 84, and all three camera inputs enter via a single DB-15 connector 86, and a manual reset button 90 is provided on each cpu board.

The processor board 54 has input/output connector 92 that allows communication with up to 64 devices. This input/output connection also communicates, via an opto-isolation module, with robot controller 26. Through this communication channel, the robot controller determines when inspections incur by controlling the indexing of the blisterpacks 30—that is, the movement of the blisterpacks through system 10. Also, when system 10 detects missing lenses, the robot controller 26, after receiving a report pack from processing subsystem 20, communicates with reject mechanism 24 and instructs that mechanism to reject the blisterpack having the package with a lens missing.

Keyboard 56 is connected to processor 54 to allow operator input thereto, and keyboard terminal 62 is used to display visually data or messages being input into the processor board. Monitor 60 is also connected to processor 54 and is provided to produce video images from the data values stored in the processor, and this monitor may also be used to display inspection results and totals. Preferably, monitor 60 is a high resolution color monitor and is controlled by a Perceptics high resolution display card, the HRD900, which is also connected to image boards 54. An RS-232 connector on processor board 54 allows terminal 62 to interact with the processor board.

Figure 10:
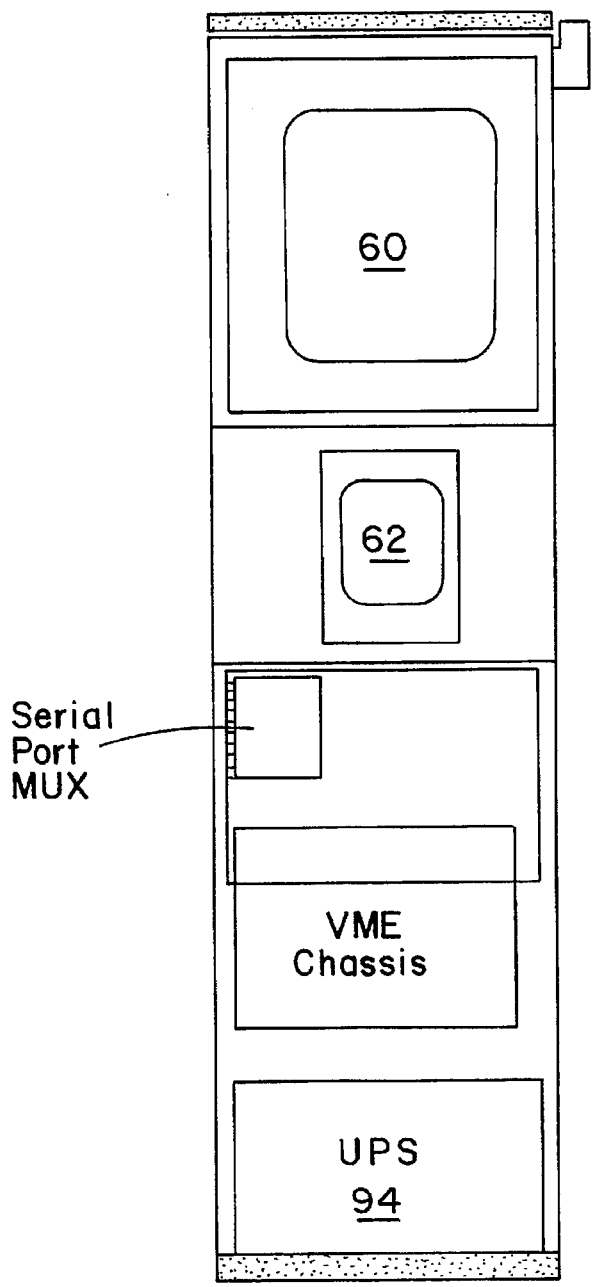
FIG. 10 shows various components of the processing subsystem arranged in a console.

The individual hardware opponents of subsystem 20 are conventional and well known by those of ordinary skill in the art. FIG. 10 shows the hardware of subsystem 20 arranged in a control cabinet. From top-to-bottom, the cabinet includes the high resolution display 60, the RS232 terminal 62, a shelf housing the keyboard, a VME chassis that holds the processor board 54, and an uninterruptable power supply 94. The control console, including the keyboard, terminal 62, high resolution display 60, and the image processor board 54 communicate with both the robot controller 26 and the cameras 42, and the robot controller, in turn, communicates to the transport subsystem 12 and the reject mechanism 24.

Figure 11:
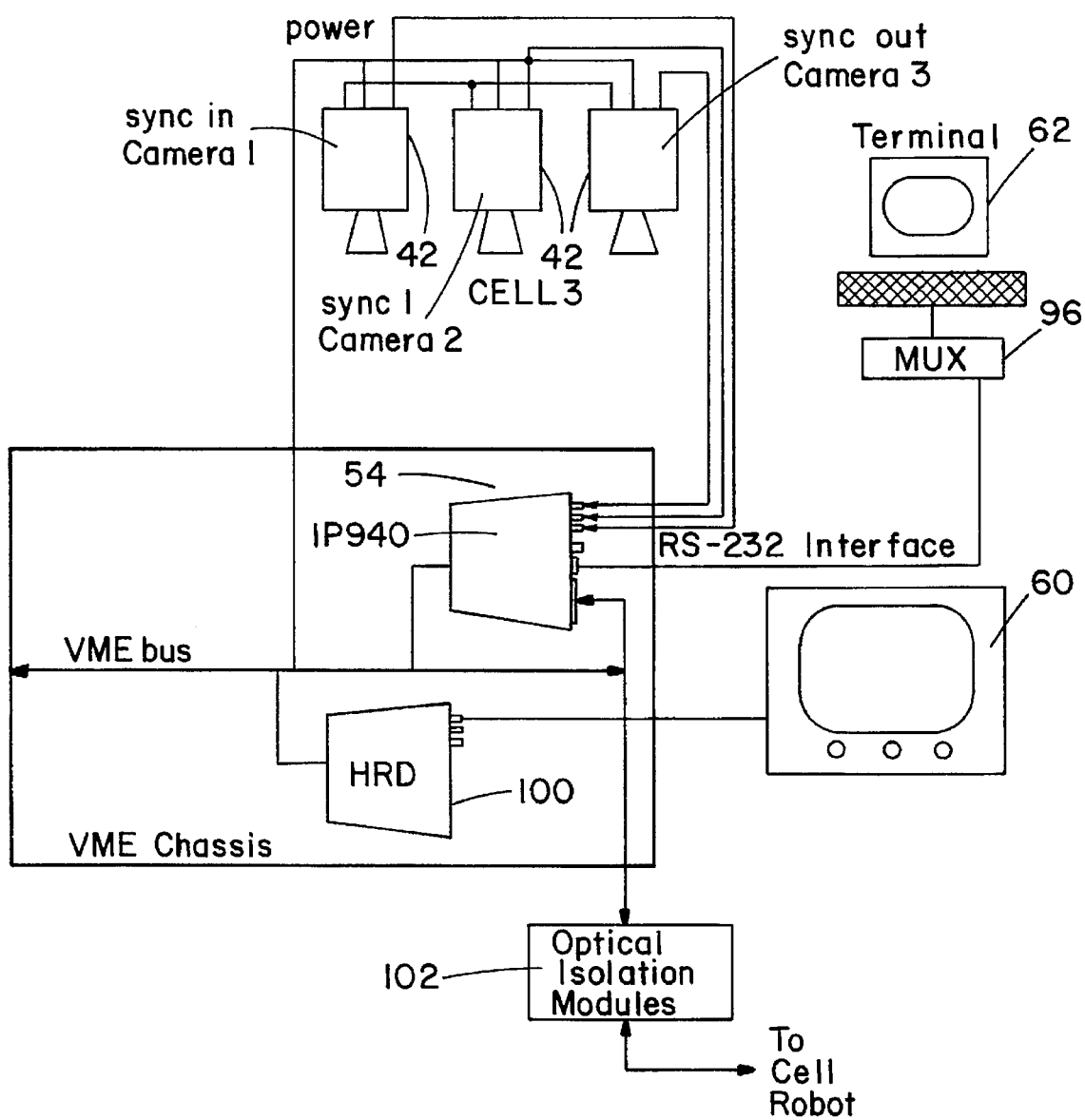
FIG. 11 illustrates various communication paths of the system shown in FIG. 1.

Communication within system 10 is illustrated in FIG. 11. Each of the cameras 42 communicates with processor board 54, and the processor board communicates with terminal 62 via the MUX 96 and an RS232 interface. Moreover, the processor board 54 is connected to the monitor 60 via the display card 100, and the processor board communicates with cell robot 22 via an optical isolation module 102.

As discussed above, each time a package 66 passes through inspection position 64, light is transmitted through the package and onto one of the pixel arrays 46, and each pixel of that one array generates a respective electric output current having a magnitude representing the intensity of the light incident on that pixel. The output current for each pixel is converted to a digital data value that is stored in an address in processor board 54, and these data values are processed to determine whether the package contains a lens.

Figure 12:
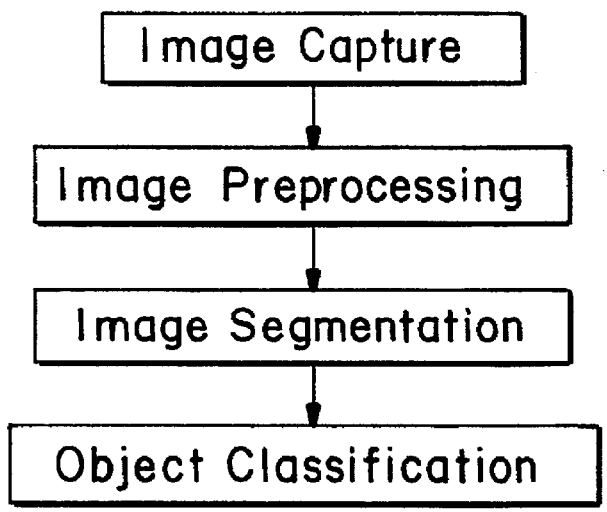
FIG. 12 outlines the major components of a preferred image processing procedure used with the inspection system of FIG. 1.

FIG. 12 shows the major components of a preferred image processing procedure to determine whether a package contains a lens. These components are, generally, referred to as image capture, image preprocessing, image segmentation, and object classification. Generally, during image capture, processor board 54 communicate with robot controller 26 to initiate the inspection process and to capture an image. Following capture of the image, the image data is preprocessed to determine where in the image, processor 54 should look for a lens. Then, objects that might be lenses are identified and measured during image segmentation; and during object classification, a decision is made as to whether one of these objects, referred to as potential lenses or lens candidates, is in fact a lens.

Image Capture & Communications Protocol with the Robot Interface

After sending an asynchronous message to the controller 26 that it is ready to inspect the next blisterpack, the image processor 54 waits for a start signal back from the controller 26. Once that start signal is received, the ready signal output line from the image processor 54 is inactivated and a package image is grabbed—that is, the grey level intensity information contained in each of the camera sensor pixels is electronically transferred to the memory of the processor board. Preferably, only one video field of 640 columns by 240 rows of pixels is grabbed and stored in the processor memory.

After the processor board 54 grabs the pixel image, and while the image is further processed, segmented, and classified in the processor memory, the robot controller 26 waits for either a fault signal or a result message from the processor board. The fault signal may be used to indicate the presence or occurrence of one or more conditions that might hinder the ability of system 10 to inspect accurately a package 66. For example, a fault signal may be generated in case the lighting from illumination subsystem 14 does not have the desired intensity, which might result in a poor image on the pixel array. This might occur when the camera 42 malfunctions, when the light bulb 36 has been turned off, or does not produce the desired intensity of light or when the transport mechanism has jammed multiple packages below the camera. To ensure that the blisterpack is not passed under these circumstances, the entire blisterpack is rejected.

If processing subsystem 20 completes the processing of the grabbed image, then the processing subsystem transmits to robot controller 26 the result of the package inspection, which is to categorize the lens that should be in the package, as either "present" or "missing." This result is transmitted over opto-isolated circuits to the robot controller.

Image Preprocessing

Figure 13:
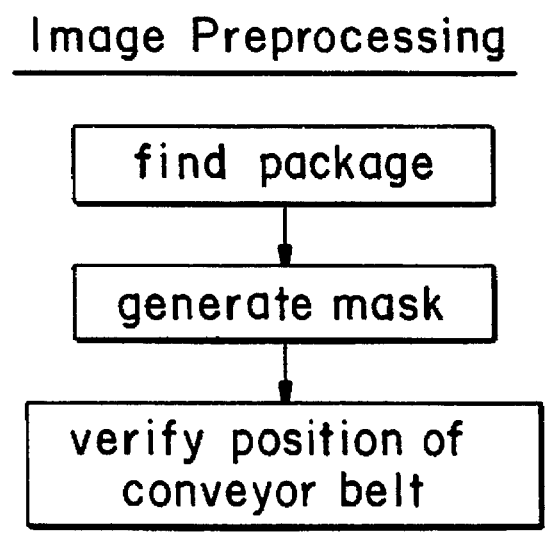
FIG. 13 outlines several image preprocessing steps.

As generally outlined in FIG. 13, during image preprocessing, the package is found, a processing mask is generated, and the position of the conveyor belt is verified. It is important to know the position of the conveyor belt because if the belt is within the processing mask placed inside the bowl of the package, the belt may be considered a lens.

a) Locating the package

Figure 14:
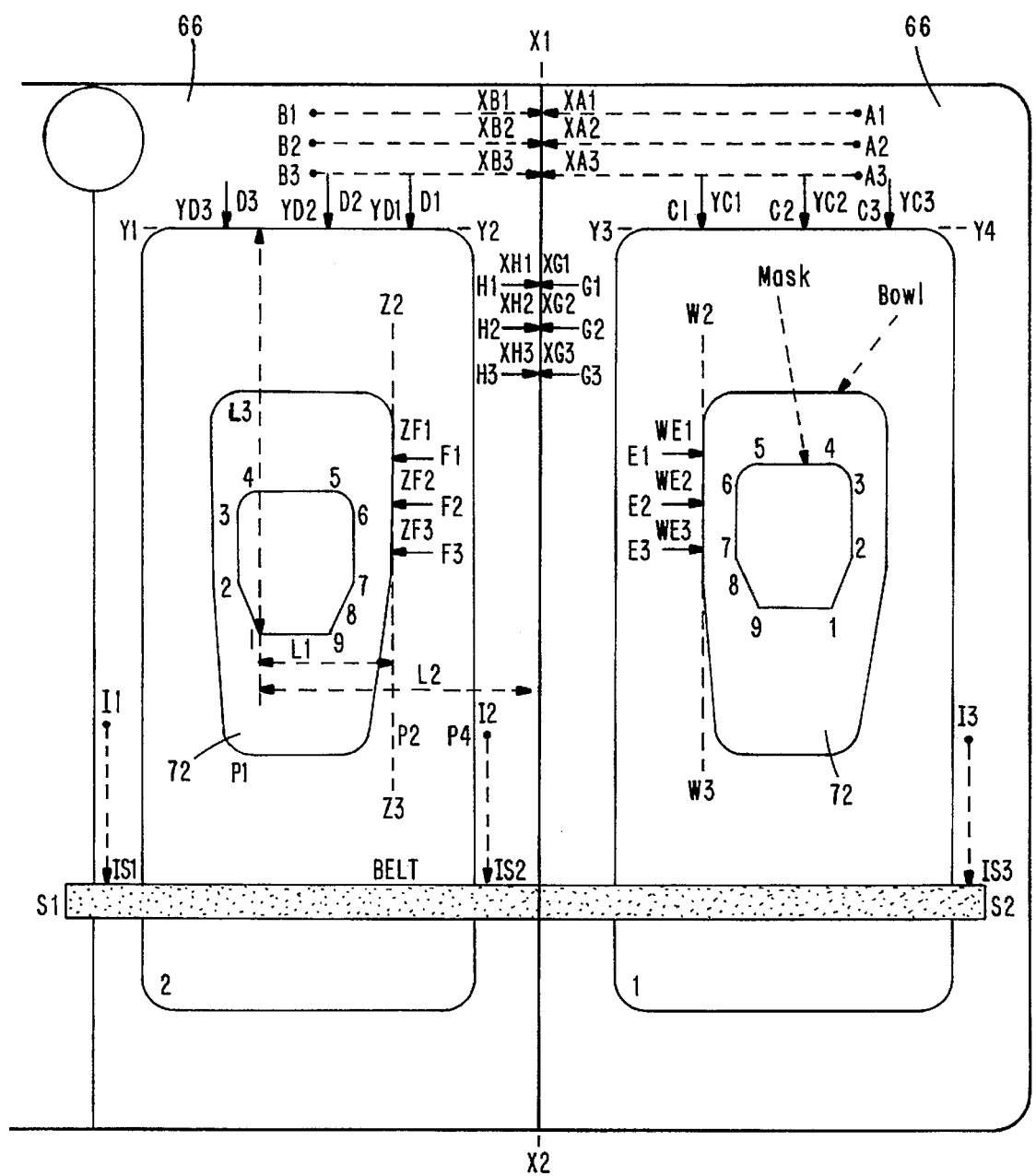
FIG. 14 illustrates a preferred scheme of search vectors used to search the image of FIG. 8 for various features.

The first task performed on the captured image is to locate the package in the image, and this is done by means of a procedure referred to as the package locator algorithm. This task is performed because, although there preferably is an image in memory, replete with all the necessary information, the processor cannot determine where to search for a lens in the image without first assessing certain image features. FIG. 14 illustrates a preferred scheme of search vectors employed in the search for package features. The first step performed is to locate the center line of the two packages in the image. This line is referred to as the package break and identified in FIG. 14 as the line X1X2. In order to find this center line, the processor searches, in opposite directions, along two search vectors A1 and B1. These vectors are actually 3×3 edge operators.

Using these operators for a given pixel of interest, the image processor 54 determines if that particular pixel is on the edge of a gradient. Equations (1) and (2) below reveal how an edge operator calculates the gradient in both the vertical and horizontal directions for each pixel $P_{i,j}$. A spatial explanation of these operators, may be understood with reference to FIG. 15, which illustrates the two dimensional mapping around the pixel of interest and its near neighbors. The subscripts i and j denote the unit vector direction of the rows and columns, respectively, in the image coordinate frame of reference. This frame of reference is the mirror image of the traditional two dimensional xy-plane, and the rows increase in the downward i-axis.

$$\text{Horizontal Operator} = P_{i+1,j+1} + 2P_{i+1,j} + P_{i+1,j-1} - (P_{i-1,j+1} + 2P_{i-1,j} + P_{i-1,j-1}) \quad (1)$$

$$\text{Vertical Operator} = P_{i-1,j+1} + 2P_{i,j+1} + P_{i+1,j-1} - (P_{i-1,j-1} + 2P_{i,j-1} + P_{i+1,j-1}) \quad (2)$$

In matrix notation, the vertical operator of Equation (1) is a 3×3 kernel, and may be used to find gradients in the left to right direction across the image. The horizontal operator of Equation (2) is also a 3×3 kernel in matrix notation, and may be used to test for gradients occurring in the top to bottom direction across the image. These kernels, which operate on the image matrix, are provided in Equations (3) and (4).

$$V_{i,j} = \begin{vmatrix} -1 & 0 & 1 \\ -2 & 0 & 2 \\ -1 & 0 & 1 \end{vmatrix} \quad (3)$$

$$H_{i,j} = \begin{vmatrix} -1 & -2 & -1 \\ 0 & 0 & 0 \\ 1 & 2 & 1 \end{vmatrix} \quad (4)$$

The forms of the matrices in Equations (3) and (4) show which is the vertical and which is the horizontal operator. Also, in these matrix forms, one side of each matrix is negative, and one side of each matrix is positive. This generates a gradient detector which is direction sensitive. Thus if $P_{i,j}$ lies on the border of an edge feature, say that of the package line X1X2 in FIG. 14, the sign of the resulting gradient value, given by Equation (5) below, indicates whether the pixel is on the left or the right side of the border.

$$\text{Gradient Value} = G_{i,j} = P_{i,j} V_{i,j} \quad (5)$$

The preferred algorithm used in the present invention employs the convention that brighter pixels have higher absolute values, within, for example, an eight bit brightness scale. All the values are between 0 and 255. Thus, for $P_{i,j}$ on the right side of a dark border, a positive gradient, $G_{i,j}$, is expected, while on the left side of that dark border, a negative gradient is expected. This ability to distinguish which side of an edge feature the search vector has encountered serves as an additional verification that the correct package border has been located. The switch in gradient sign in the vector search path indicates border presence.

Accurately locating the package border improves the effectiveness of the inspection. To elaborate, in order to minimize the amount of memory used in the later stages of the processing, only a portion of the package image is searched for a lens. This portion of the package image is the area thereof that is covered by a mask having a preset size and shape and that, in effect, is superimposed on the package image. The mask itself is positioned on the package image by locating the mask preset distances from certain package features or borders. If the mask is incorrectly placed in the package image, then a normal package feature could be mistaken for a lens. Proper placement of the mask depends on accurately locating the package features used to position the mask, and, with the preferred embodiment of the search process, on the accuracy of the search along vectors A1 and B1.

Sometimes a single search vector may not yield positional data for the package feature with the desired preciseness. For example, if a water drop falls onto the blisterpack so as to intercept either of the converging search vectors A1 and B1, then the processor board 54 might not precisely determine the thickness of the line X1X2. For that reason, redundancy is built into the search algorithm. For example, three pairs of search vectors may be employed to find the edges of the line X1X2. If the first pair A1, B1 encounters interference from a water drop, then the image processor uses a second pair of vectors A2, B2. If the second pair fails to identify the package edge, then the Q algorithm uses a third pair A3, B3 to find that edge.

In order to determine whether one pair of these vectors is sufficient to find line X1X2, the difference between the end points of vectors A1 and B1 may be compared to a threshold for the expected thickness of the line X1X2. For example, if the endpoints of A1 and B1 are spaced apart by greater than four pixels more than the expected thickness of line X1X2, then the second pair of search vectors may be activated. It may be noted that horizontal and vertical pixel resolution is different in this vision application, so vertical tolerances may differ from the horizontal tolerances in pixel magnitude due to sensor geometry.

After an initial determination is made of the location of line X1X2, the location of that line is double checked by searching along a second set of vectors G1, G2, G3, and H1, H2, H3. The search along vectors Hn and Gn is conducted in the same way as the search along the vectors An and Bn. However, the Hn and Gn vectors may be placed more accurately than the An and Bn vectors—that is, the search along the Hn and Gn vectors may start closer, than the search along the vectors An and Bn did, to the package edge—since more is known about the package location at that point, and in particular, more is known about the location of the line X1X2.

The position of the top of the package—and specifically, the position of the top of the package along a y-axis—is found by searching downward along one or more vectors, such as the YDn and YCn vectors shown in FIG. 14. After finding the horizontal edge to the package top, a first vertical or longitudinal edge of the cavity or well 72 of the package is found. In FIG. 14, this edge is designated as Z2Z3, and it may be found by searching along one or more search vectors, such as the Fn vectors shown in FIG. 14. The starting points of these Fn vectors can be determined very accurately, due to the known positions of X1X2 and Y1Y2; and as shown in FIG. 14, the starting location for the Fn vectors is between two closely spaced package features.

b) Setting the mask area inside the bowl

Once the line segments Y1Y2 and Z2Z3 are found, a first point of a processing mask or template is calculated. This first point of the mask is offset a respective given distance from each of the lines Y1Y2 and Z2Z3; and more specifically, a Y offset is added to the row coordinate of the Y1Y2 line, and a Z offset is subtracted from the column coordinate of the Z1Z2 line. In FIG. 14, this Y offset is labeled L3, and this offset is referred to as the parameter "A1_row_ofs"; and the Z offset is labeled L1 in FIG. 14 and is referred to as the parameter "A1_col_ofs." Preferably, these parameters are user accessible constants—that is, a user has access to and can change the values of these constants.

After this first mask point is determined, a plurality of additional points that define the mask are determined. For example, as illustrated in FIG. 14, nine points may be used to define the mask. The locations of the eight additional mask points may be determined, for instance, by storing nominal address locations for all of the mask points in the memory of processor 54, determining the offset between the actual and nominal locations of the first mask point, and then adding that same offset to the nominal locations of each of the additional mask points. Equations (6) and (7) below mathematically express this procedure for determining the second point of the mask.

$$
\begin{aligned}
A2_{row} &= A2_{row}\epsilon BBRAM - (A1_{row} - A1_{row}\epsilon BBRAM) & (6) \\
&= A2_{row}\epsilon BBRAM - A1_{row} + A1_{row}\epsilon BBRAM \\
A2_{col} &= A2_{col}\epsilon BBRAM - (A1_{col} - A1_{col}\epsilon BBRAM) & (7) \\
&= A2_{col}\epsilon BBRAM - A1_{col} + A1_{col}\epsilon BBRAM
\end{aligned}
$$

Similar equations are used to determine the row and column locations of each of the additional mask points, which in the preferred embodiment of the.

Also, the pixels on a nominal perimeter of the mask may be stored in the processor memory. This nominal perimeter may be determined mathematically from the nominal addresses of the nine points that define the mask. Alternatively, a graphical program may be used to enter this nominal perimeter into the processor memory. For instance, a display may be produced on input monitor 62 showing the locations of the nine points that define the mask, and a cursor may be moved among those points, tracing the mask perimeter. As the cursor moves from pixel to pixel, the address of each pixel on the mask perimeter, as traced by the cursor, may be added to the processor memory. The actual perimeter of a mask that is superimposed on any actual image, can then be determined by adding to each pixel address of the nominal mask perimeter, the above-mentioned y and z offsets calculated for that particular image. algorithm are designated as points 3 through 9.

c) Verifying the belt location

As shown in FIG. 14, an outline of the conveyor belt 32 may appear on the image formed on the pixel array 46. If the belt 32 intrudes into the mask area, then the belt may be considered as a lens by the image processor 54. In order to prevent this from happening, the mask area is made smaller than a maximum allowable area, so as to provide a tolerance for the position of the conveyor belt. Also, the position of the belt is detected in the image by searching along search vectors such as those shown at In in FIG. 14. Once the search along the vectors In identifies points, or pixels, on the top edge of the belt, those pixels are fit with a line. This line represents the top edge of the conveyor belt; and if this line crosses the mask boundary at any point, then an error signal is generated and the blisterpack is failed. Preferably, this condition only occurs in case the belt 32 moves from its normal position.

Image Segmentation

Next, in a process referred to as segmentation, the area of the image inside this processing mask is divided into smaller parts and objects within that image area are identified. With the preferred algorithm used in system 10, the image is segmented according to abrupt changes in grey level. Singular points or lines are not as important to find as are whole edges of objects.

a) Edge detection

In vector representation, the image seen by, or produced on, the camera pixel array 46 can be described as a function of the row and column position on the sensor. In order to differentiate objects from background noise in the image, a gradient operator is used. The preferred algorithm looks, first, for edges within the image area and then analyzes those edges to determine if one might be the edge of a lens.

The preferred method employed to look for edges inside the mask area is an approximation of a two dimensional partial differentiation of the image array of luminance values, or grey levels, of the image function f(x,y). The two dimensional gradient of the image can be represented by the following vector formula.

$$G[f(x,y)] = \begin{vmatrix} G_x \\ G_y \end{vmatrix} = \begin{vmatrix} \frac{\partial f}{\partial x} \\ \frac{\partial f}{\partial y} \end{vmatrix} \quad (8)$$

The magnitude of the gradient vector can be approximated by the sum of the absolute values of the two partial derivatives of the image function.

$$G[f(x,y)]_{magnitude} = \sqrt{G_x^2 + G_y^2} \approx |G_x| + |G_y| \quad (9)$$

A horizontal and vertical operator, known as the Sobel operator, can be obtained by substituting the vertical and horizontal edge operators $V_{i,j}$ and $H_{i,j}$ for $G_x$ and $G_y$.

Sobel Operator (Horizontal+Vertical)=$|V_{i,j}|+|H_{i,j}|$ (10)

$V_{i,j}$ and $H_{i,j}$ can themselves be determined from the 3×3 kernel operators given in Equations (3) and (4).

The absolute values of $V_{i,j}$ and $H_{i,j}$ are used by the Sobel operator, and therefore this operation is not sensitive to the direction of the gradient with respect to the point of interest $P_{i,j}$. It is not necessary for the Sobel operator to be direction sensitive because the lens edges are so varied in their position and direction that no preferred geometry exists to be detected. Hence, none of the simple techniques used in semiconductor industry, such as wafer inspection using a golden image approach, would work effectively with a contact lens. Full image segmentation and classification, not simple pattern matching, is required to detect a lens in package 66.

The use of the processing mask saves greater than a million mathematical operations per image, and allows the inspection of the blisterpacks 30 to occur within a relatively small amount of time. To elaborate, the Sobel operator requires that two 3×3 kernels be added together for every point in the image. A single 3×3 kernel operating on or convolving with a 640×240 image matrix would require 1,398,276 operations,—that is, 9 operations on each of 642×242 memory locations. The processing mask is placed where the lens is expected to exist, and for example, may occupy less than 3,200 pixels, which need fewer than 31,000 operations per 3×3 kernel. The Sobel edge operator actually performs 19 operations per pixel, which totals slightly more than 64,500 operations for the 3,200 pixels covered by the mask. As will be appreciated by those of ordinary skill in the art, in order to use effectively this comparatively small pixel area to determine whether a package has a lens, it is important that the processing mask be accurately located. This in turn requires that the package features that are used to position the mask, be accurately located.

b) Object tracking

Once the edges of the objects within the mask area are identified, the algorithm organizes the edges into objects. Any suitable connectivity procedure may be used to do this, and for instance, the edges may be organized into objects using a technique that may be referred to as eight connectivity analysis. In this technique, when a first pixel is found that is an edge of a particular object, the eight immediate pixel neighbors of that pixel are searched, in a uniform direction, for a second edge pixel. If a second edge pixel is found, it is considered to be on the edge of the particular object, and, also, the process is repeated and the eight immediate neighbors of this second edge pixel are searched, in the uniform direction, for a third edge pixel. This process is repeated—a procedure referred to as tracking the edge or tracking the object—until either an end of the edge is found, or the edge formed by these identified edge pixels forms a closed loop, and more specifically, that edge returns to the first edge pixel of the particular object.

Figure 16A:
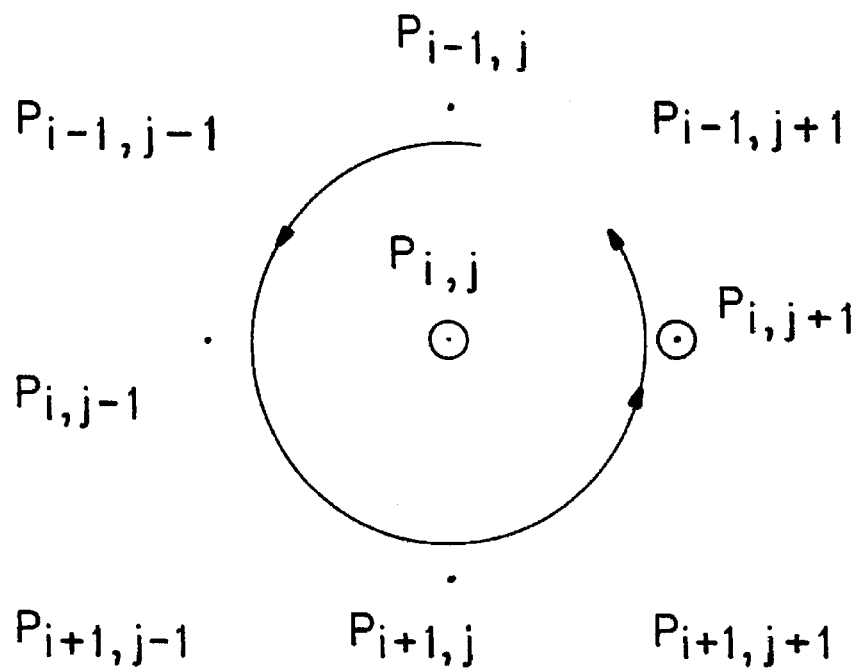
FIGS. 16A and 16B illustrate a pixel searching technique used in the preferred processing procedure.
Figure 16B:
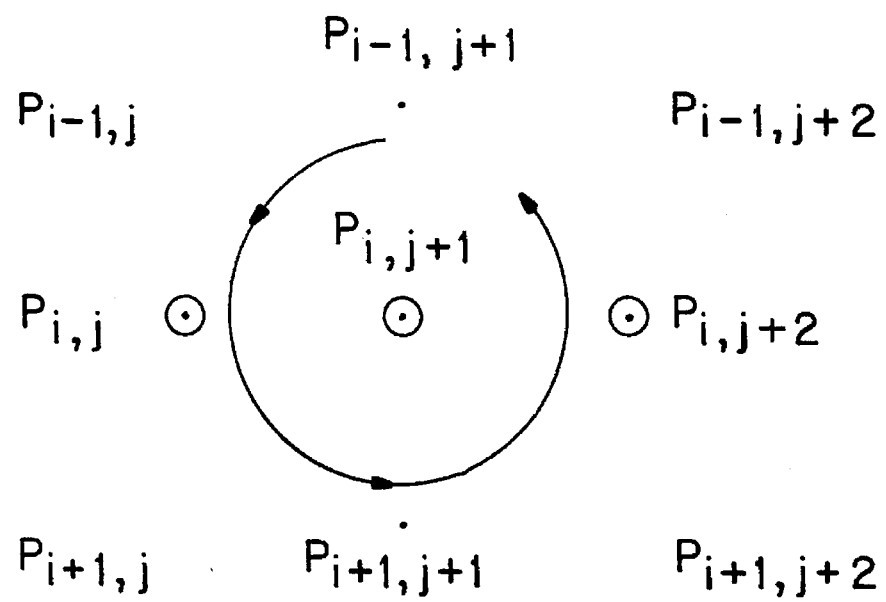

FIGS. 16A and 16B illustrate this eight connectivity analysis in greater detail. In FIGS. 16A and 16B, each pixel is represented by a point, to better illustrate the search around each pixel. FIG. 16A shows a first pixel, $P_{i,j}$, that has been identified as being on an object edge. The eight immediate pixel neighbors are searched, in a counterclockwise direction starting from the pixel immediately above $P_{i,j}$, for a pixel that has a grey level above a predetermined threshold. The first pixel that is found that meets this test is considered as the next edge pixel, which in the example of FIG. 16A is pixel $P_{i,j+1}$.

At the next step, illustrated in FIG. 16B, the eight immediate pixel neighbors of $P_{i,j+1}$ are searched—again, in a counterclockwise direction starting from the pixel immediately above $P_{i,j+1}$—for a pixel that (i) has a grey level above the predetermined threshold, and (ii) was not the pixel at the center of the immediately preceding search. The first pixel that is found that meets this test is considered as the next edge pixel; and in the example shown in FIG. 16B, that next edge pixel is $P_{i,j+2}$. This tracking process continues until either the search returns to pixel $P_{i,j}$, or a search around a given pixel fails to identify any next edge pixel.

With the above-described procedure, the pixels that are identified as being on the edge of a specified object form an edge or outline of what is referred to as the tracked object, and the shape of the tracked object may be different from the shape of the original image object that was the basis of the tracking process. This is the result of the fact that, in the above-described eight connectivity analysis, a pixel may be identified as an edge pixel even though it is not actually on the edge of the image of the object. From this first off-edge pixel, the algorithm may continue to track off the actual edge of the image of the object until returning to that actual edge.

More specifically, this is due to the fact that the contrast, or the difference in the grey values, between the edge of the image of an object, and the areas of the image immediately adjacent the object edge, varies along the object edge. When that contrast is high—in which case the edge of the object is described as strong—the eight connectivity analysis tracks along the object edge. However, when that contrast is low—in which case the edge of the object is referred to as weak—the eight connectivity analysis may identify an edge pixel as a non edge pixel.

The possible difference between the actual edge of an image of an object and the tracked edge may be further understood with reference to FIGS. 17A–17D and 18A–18D. FIGS. 17A–17D show four typical objects that may be detected in the lens packages, and FIGS. 17A–17D show the tracked edges that are obtained by tracking along the edges of the objects of FIGS. 17A–17D using the above-discussed eight connectivity analysis.

Figure 17A:
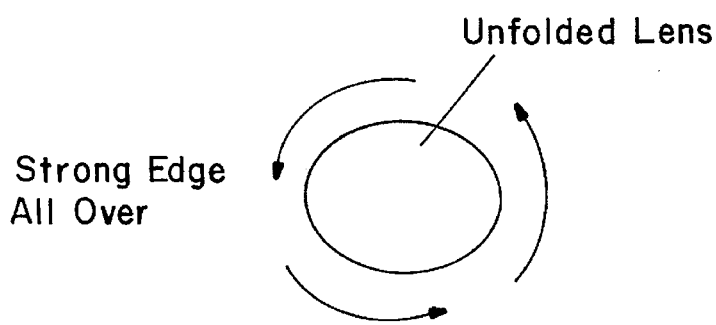
FIGS. 17A–17D show four objects that may be encountered in a package inspection.
Figure 17B:
Figure 17C:
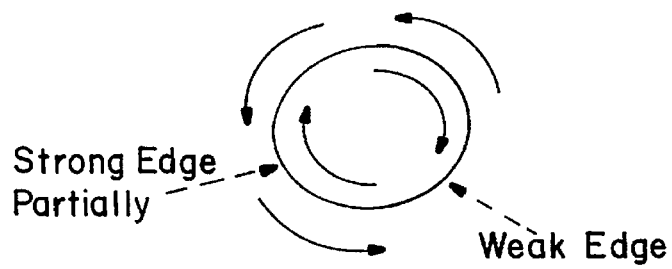
Figure 18C:
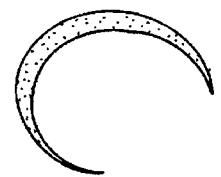
Figure 17D:
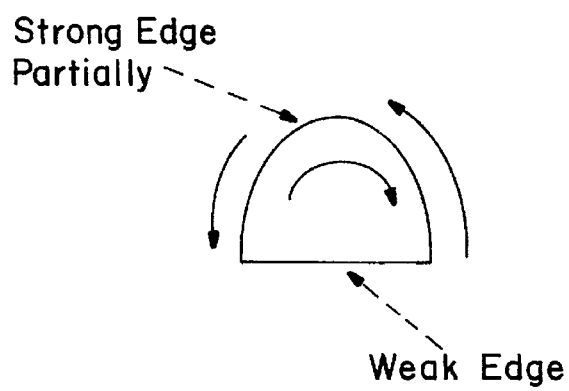
Figure 18D:
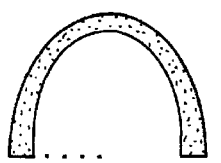

All of the objects shown in FIGS. 17A–17D are images of lenses; however, FIGS. 17A and 17C show images of unfolded lenses, and FIGS. 17B and 17D show images of folded lenses.

Also, the entire edges of the objects shown in FIGS. 17A and 17B are strong; while the edges of the objects shown in FIGS. 17C and 17D have strong and weak portions. Because of their shapes and the strength or weakness of their edges, the objects illustrated in FIGS. 17A–17D are referred to, respectively, as an unfolded lens, a folded lens, an unfolded lens with a weak edge, and a folded lens with a weak edge. Preferably, as illustrated in FIGS. 17A–17D, the object edges are tracked counterclockwise. Some segments of the lens edges shown in FIGS. 17A–17D are lost or eliminated in tracking, resulting in the crescent or arched shaped tracked object shown in FIGS. 18C and 18D. Only lenses found by the Sobel operators and resulting in gradients greater than a given value referred to as "edge_thr" are kept in the memory of processor 54. Lenses partly positioned outside of the mask area will not exhibit an edge feature at the border of the mask.

Figure 18A:
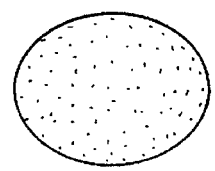
FIGS. 18A–18D show outlines of the four objects of FIGS. 17A–17D that are formed by the pixel searching technique.
Figure 18B:
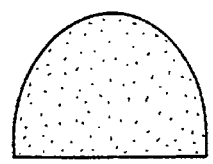

Because the entire edges of the objects shown in FIGS. 17A and 17B are strong, the eight connectivity analysis tracks along the actual edges of the objects over the entire edges thereof, as shown in FIGS. 18A and 18B. The eight connectivity analysis also tracks along the strong portions of the edges of the objects shown in FIGS. 17C and 17D; however, when this connectivity analysis reaches a weak portion of the edges of these objects, the analysis tracks off those actual object edges, along the image edges formed by the stronger gray level gradients.

Figure 19:
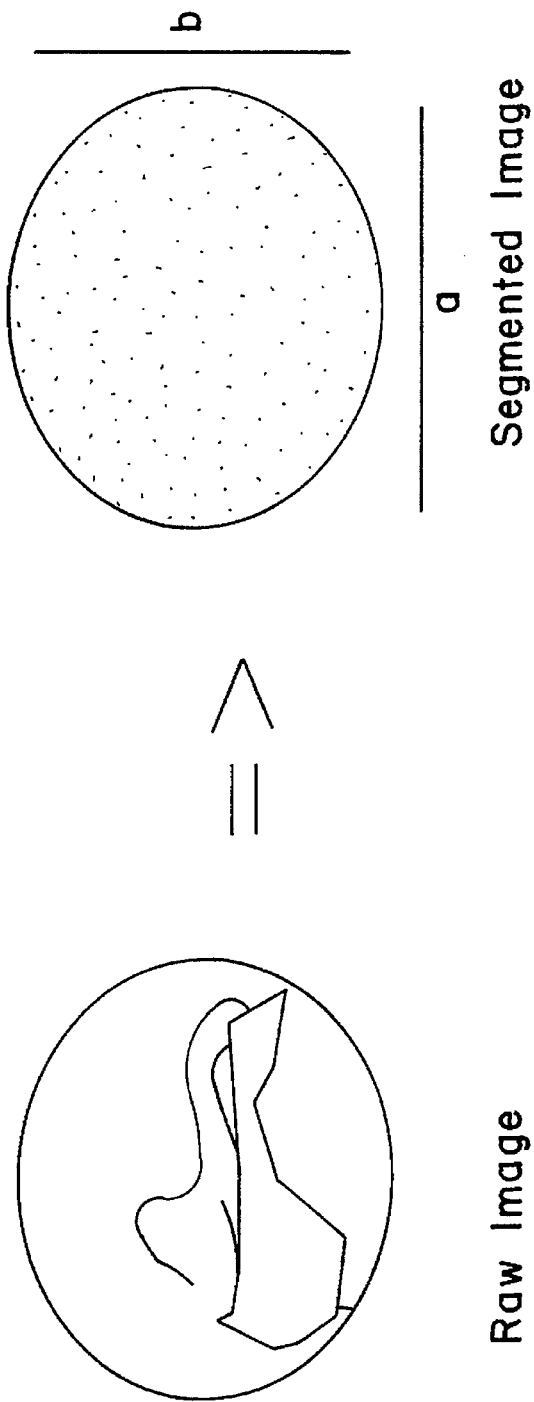
FIG. 19 schematically depicts the way raw images are processed by the image processing procedure.

When a lens is released by robot 22, the lens may strike package 66 preferentially on one side. The free edge of the lens that is still in flight, still conserving angular momentum, may fold over on the portion of the lens attached to the package. FIG. 17B shows the edge of such a folded lens as it may appear in the package image formed on one of the pixel arrays 46, and FIG. 18B shows the outline that is formed as the lens edge is tracked by the object tracking routine. As generally illustrated in FIG. 19, in the eight connectivity algorithm, only the general outline of the lens shape is determined. The shapes are filled in during the next step, object labeling.

A second type of image distortion results in the segmentation of a crescent shaped object, even though the lens is wholly within the mask field of view. Object tracking will fail to follow weak edges. Excess water on the lens, for instance, may tend to smooth the contact between lens and package. This in turn lessens the contrast visible at the wet edge of the lens. A similar distortion occurs if a lens lies partially outside the mask boundary. Where the lens crosses the spatial boundary of the mask no physical lens edge exists to refract light differentially from one pixel to another. Thus, there is little edge signal to find. There are also smaller amplitude fluctuations in brightness in random areas of the lens interior due to wrinkles in the lens, and these may be tracked instead of weaker edge signals. As a result, opposite sides of the lens may not be connected by tracking, and an arch shape is formed.

The weak edges of the lenses could be distinguished by the processor board 54 if the definable parameter "edge_thr" was set lower. However, illumination subsystem 14 is preferably designed so that the lighting therefrom produces the maximum contrast for all objects under the camera, and lower "edge_thr" values would cause the algorithm to identify as objects more items or features from the package surface detail.

Object tracking is completed once the original starting point is reached again for the given object. The processor board 54 searches the mask area for any pixel with a sufficiently high gradient outcome from the Sobel operation. Once one such pixel is found, processor 54 finds all such neighbor pixels, and the processor continues searching neighboring pixels until the first pixel is located again. An object is then considered to be found. The image processor 54 repeats this cycle for all pixels within the mask boundary.

c) Object labeling

All found objects are then labeled. During the labeling process, all pixels inside each object are given the same predefined grey level, which preferably is different for each object. These predefined grey levels may correspond to a series of identifying colors identified in a display look up table on the video signal transmitted to the monitor 60. Generally, to assign the grey level values to the pixels inside each object, processor 54 identifies the boundary condition for the object and then gives each pixel inside that boundary the appropriate grey value. Any standard morphological routine may be used to assign the grey values to the pixels inside each object, a process referred to as filling in the object; and because each object has a closed perimeter, the morphological routine is straightforward.

During object labeling, which is the last step in the segmentation process, each object is given several numerical identifiers. First, the objects are numbered in the order in which they are encountered; and the above-mentioned color values that are assigned to the pixels inside each object correspond to or are determined by the number of the object. Numerical data is also generated for parameters referred to as perimeter, area, aspect ratio, and complexity.

The perimeter of an object is defined as the total number of pixels encountered on the edge of the object. With reference to FIG. 18, the aspect ratio of an object is defined as the ratio a/b, and the area of an object is defined as the product a·b, where a and b are the width and height, respectively, of the object. The width of an object may be defined as the length of the longest line segment that can be drawn across the object in a direction perpendicular to the line X1X2, and the height of an object may be defined as the length of the longest line segment that can be drawn across the object in a direction parallel to the line X1X2. As will be understood by those of ordinary skill in the art, the parameter referred to as area is not intended to indicate precisely the size of the object; and instead, this parameter more closely indicates the size of the smallest rectangle, referred to as a bounding box, that completely encloses the object.

The complexity parameter is a measure of the complexity of the shape of an object, and more particularly, is an indication of the relative frequency of directional changes in the boundary of the object. For example, complexity may be defined as the ratio of $p^2/A$, where p is the length of the perimeter of the object and A is the above-discussed area value of the object. The aspect ratio, area, and complexity of an object may be expressed mathematically as follows:

$$\text{Aspect Ratio} = \frac{a}{b} \qquad (11)$$

$$\text{Area} \approx (\text{Bounding Box Size}) = a \cdot b \qquad (12)$$

$$\text{Complexity} = \frac{p^2}{A} \qquad (13)$$

Each object is thus given a number, color, and four additional numerical descriptors. The number and color of an object are used for identification purposes; and the area, perimeter, aspect ratio, and complexity values assigned to an object are used for classification purposes.

Multiple Object Classification

Each object found inside a mask is considered to be a lens candidate; and after object segmentation is complete, each lens candidate object is processed, or classified, according to a classification algorithm. Preferably, the classification of all the objects found within the mask is accomplished with a linear decision based classifier.

Figure 20:
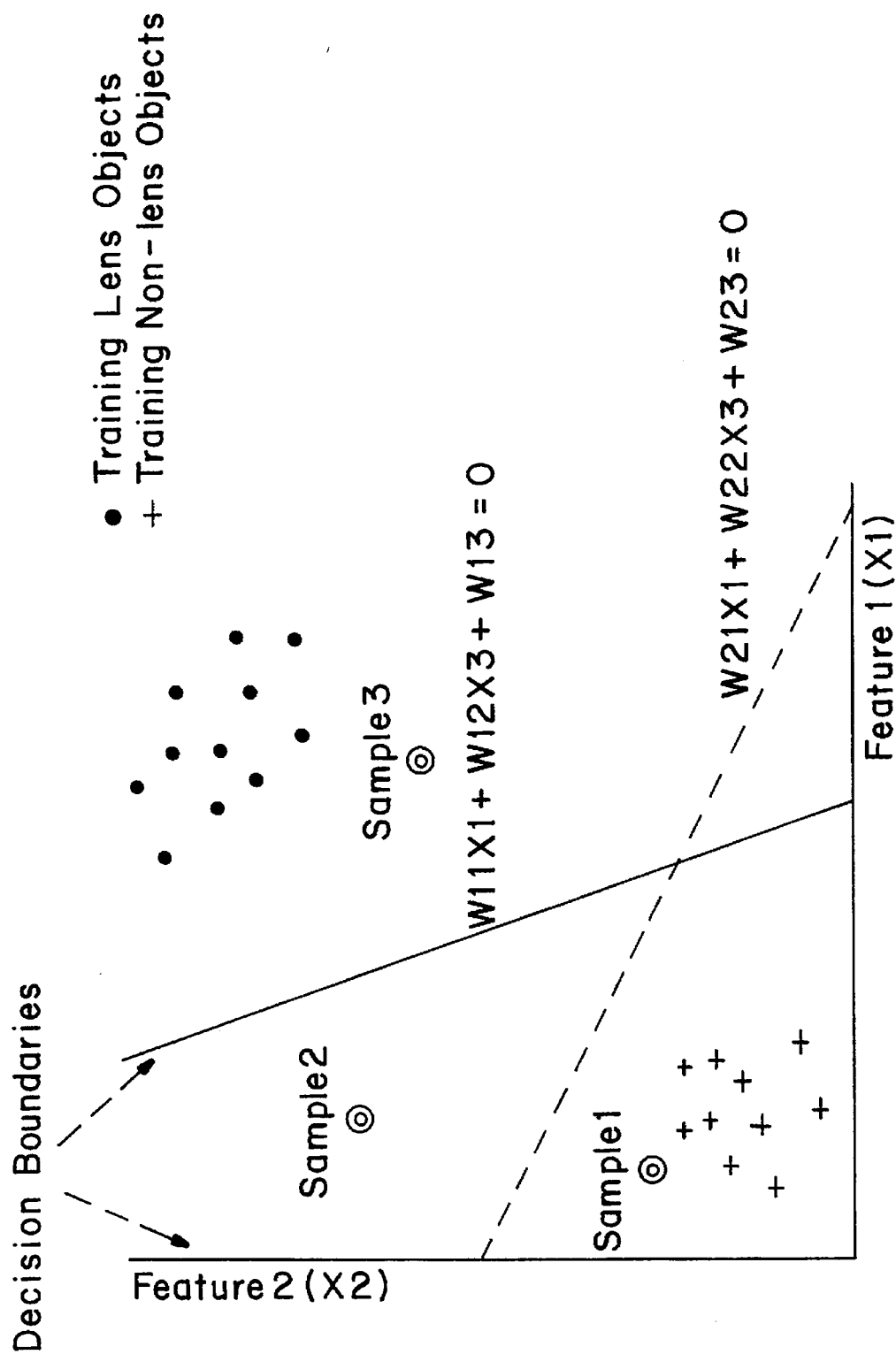
FIG. 20 illustrates a two dimensional linear classifier to distinguish between packages that have lenses and those that do not.

Many suitable linear decision based classifiers may be employed in the practice of this invention; and, for example, FIG. 20 shows a simple two dimensional linear classification. More specifically, FIG. 20 shows plots of two groups of objects on an x-y graph. The first group of these objects, identified as sample no. 1, are not lenses, and another group of objects, identified as sample no. 3, are lenses. The x and y axes of FIG. 20 could represent any two of the above-mentioned, or additional, parameters of the objects, that cause the plots of the two groups of objects to form respective, spaced apart clusters.

The clustering of data values based upon the numerical descriptors, as illustrated in FIG. 20, can occur if representative images are segmented. Representative images yield such clustering only if the numerical descriptors correlate to independently distinguishable features of the objects under test. For example, the axis of Feature 1 in FIG. 20 could represent size.

As FIG. 20 illustrates, a line can readily be drawn separating the objects of sample number one from the objects of sample number three. In fact, at least two separate and well defined decision boundaries satisfy requirements for the clustered data—that is, clearly distinguish between lenses and non-lenses—and the data plotted in FIG. 20 does not clearly show which of these decision boundaries is best. Samples 1 and 3 appear as though they are correctly classified by both boundary lines, i.e., they are on the correct side of each line. There is, though, significant area between the two boundary lines, and an object, identified as sample no. 2, could be plotted between the two boundaries, and not clearly belong to either of the two shown clusters of plotted objects. Sample 2 could be, for instance, a large water drop or a folded lens. Because of this, in the preferred embodiment of the object classification procedure, more information is used to determine the linear classification.

Initial tests on a prototype system revealed that approximately 70 percent of the decisions were correct if the decisions were based solely on the area and perimeter descriptors. A multidimensional decision function increases the accuracy of the decisions. In order to organize the classification most efficiently, a perceptron based derivation of the decision function was used. The decision function is preferably a four dimensional function, described by the following equation.

$$D_i = \omega_a A_i + \omega_p P_i + \omega_r R_i + \omega_c C_i + \omega_5 \qquad (14)$$

Equation (14) is called the decision function because it classifies each object i, for all objects inside the mask boundary. The object descriptors A, P, R, and C, are the respective area, perimeter, aspect ratio, and complexity values measured or determined for each object in each image during object labeling. $\omega_a$, $\omega_p$, $\omega_r$, $\omega_c$, and $\omega_5$ are referred to as classification weighting vectors. $\omega_a$, $\omega_p$, $\omega_r$, and $\omega_c$ represent weights for, respectively, the area, perimeter, aspect ratio, and complexity values assigned to the object, and $\omega_5$ is a constant value.

Values may be assigned to the weighting vectors such that if $D_i$ is greater than zero, then object i is labelled a non-lens, while if $D_i$ is less than or equal to zero, then object i is labelled a lens. Expressed mathematically, this condition is:

$$\begin{aligned}\text{Object Class} &= \text{Non-LENS if } D_i > 0 \\ &= \text{LENS if } D_i \leq 0\end{aligned} \qquad (15)$$

Preferably, values are assigned to the weighting vectors so that more than 99 percent of the decisions are accurate.

In order to correctly identify the Object Class as lens or non-lens, for thousands of objects, with overlapping descriptor boundaries, the vector constants of Equation (14) are modeled on a computer using a Perceptron algorithm. Perceptron algorithms are known in the art, and any suitable algorithm may be used to determine values for the weighting vectors in Equation (14). For example, Perceptron algorithms are discussed in Chapter Five of "Pattern Recognition Principles," by Tou and Gonzalez, published by Addison-Wesley Publishing Company (1974). Generally, the Perceptron algorithm is a deterministic trainable pattern classifier. No assumptions are made concerning the statistical relationship between the mathematical descriptors of the objects to be classified. The Perceptron algorithm is deterministic, in that it assumes a solution exists.

The data presented are separated before computation into two classes. The data patterns of the non-lens descriptors are all multiplied by −1. For example, if $x_i$ represents a set of training patterns containing the numerical descriptors A, P, R, and C, then the algorithm yields a solution weight vector $\omega^*$, where $\omega^* x_i > 0$, and $\omega^* = \omega_a$, $\omega_p$, $\omega_r$, $\omega_c$, and $\omega_5$.

Figure 21:
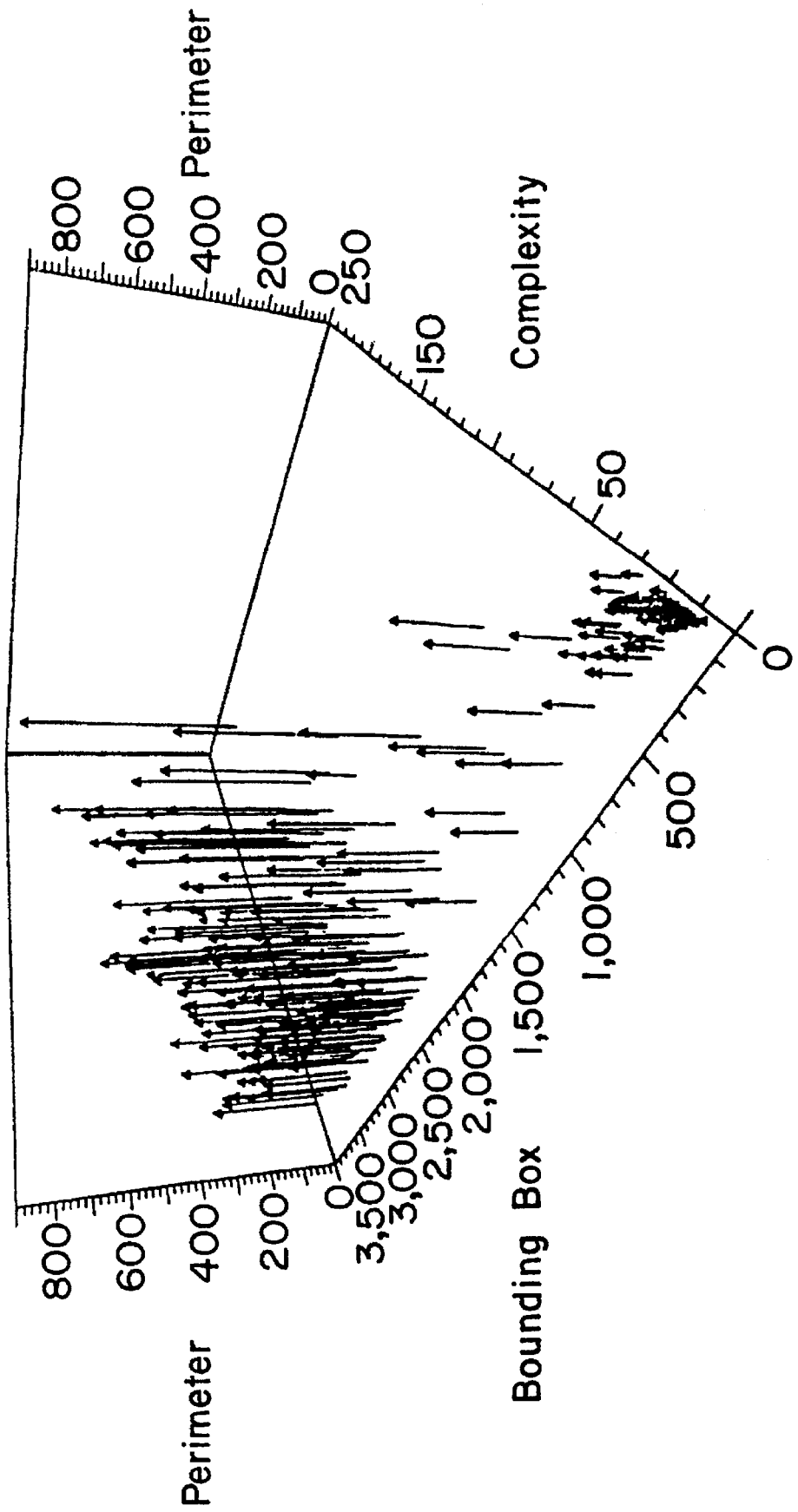
FIG. 21 shows a multi-dimensional classifier for distinguishing between packages that have lenses and those that do not.

FIG. 21 exemplifies the complexity of the real data from the lens verification system. This Figure represents only 300 data points, and only in 3-dimensional space. Though the images from which the data of FIG. 21 were derived were representative of ideal lenses and water drops, there are no easily definable clusters. In order to improve the accuracy of the classification, a multi-dimensional surface, such as a four or five dimensional surface, is preferably used as the boundary.

Once appropriate values for $\omega_a$, $\omega_p$, $\omega_r$, $\omega_c$, and $\omega_5$ are determined by the Perceptron algorithm, the decision function is permanently entered into the memory of the processor board 54. $D_i$ is then used to classify every object encountered within the mask regions of every image.

The proper characterization of the objects, their numerical descriptors, and ultimately the modeling of the decision function classification weighting vectors help the system 10 achieve a very high degree of accuracy. In order to improve the accuracy of the model, the Perceptron algorithm uses a reward and punishment concept. Essentially, all the data patterns from the training set are run through the $k^{th}$ $\omega^*$ vector model and if the decisions are not correct, $\omega^*$ is incremented by a factor c for the $(k+1)^{th}$ attempt. The punishment is that the computer has to recalculate, and the reward is finishing the calculation.

In order to determine one set of weighting factors, eighty package images were analyzed and processed. Of those eighty packages, forty contained lenses, and forty did not have lenses. Water drops of various sizes were placed on the forty packages that did not have lenses. The numerical descriptors for each object found within the processing masks placed on the images were recorded, and the whole 80 image array of numerical descriptors was run through the Perceptron classifier algorithm. These Perceptron calculations resulted in a vector of the form of Equation (14). Substituting the results of the Perceptton calculation for the classification weighting vectors, $\omega_a$, $\omega_p$, $\omega_r$, $\omega_c$, and $\omega_5$, yielded Equation (16).

$$D_i = (4352)A_i + (19112)P_i - (334545.75)R_i - (129398.36)C_i - 731538 \quad (16)$$

In a test, image processor 54, employing equation (16), was used to classify each object within the masks of several thousand package images. The processor identified each package as being in one of two classifications, identified as "missing" and "present." Specifically, each package was placed either in the present or missing category depending on whether the processor, respectively, found or did not find a lens in the package. Each of these package images was also observed on monitor 60 by a human operator, and each classification by processor 54 was characterized by the human operator as either correct or incorrect. This results in four possible classification outcomes, missing-correct, missing-incorrect, present-correct, and present-incorrect.

Of 6516 packages inspected, processor 54 correctly identified 272 as missing lenses, incorrectly identified 64 as missing lenses, and incorrectly identified 4 as having lenses.

Additional experiments were performed to improve the verification system; and, specifically, additional package images were analyzed and processed to collect additional data on the numerical descriptors. A sample of these additional data are shown in the tables of FIG. 22. In these tests, each object found in the masks was classified, based on the pattern of the object, into one of a multitude of groups, referred to as round, pac-man, folded and on-side. Borderline objects, which could be argued to fall into more than one group were excluded from the data.

Each table of FIG. 22 includes five columns of information. The first column is the bounding box size, the second column is the complexity, the third column is the aspect ratio, the fourth column is the perimeter, and the fifth column is a type code, describing the object.

In these tables, the typical round lenses are represented by the number one in the far right column. Folded, on-side, and pac-man lenses are represented by the codes F, OS, and P respectively. A folded lens can be anywhere within the mask, and can be folded once or twice. An on-side lens appears on the edge of the mask, and is not completely visible. Lenses that fall within the pac-man description have the general shape of a round lens which has a weak edge. The weak edge, when segmented, appears as a missing area in the shape of a triangle. Images of water drops are denoted by the code W. When this data was processed by the perceptron algorithm, all codes were replaced with numeric values. F, OS, and P were replaced with the number one, and the code for water drops was replaced by a negative one.

In these additional experiments, numerical descriptors were compiled for 328 objects, half of which were lenses and the other half of which were representative of water drops. These data were input into a Sun Microsystems Sparcstation 1, which compiled and ran the calculations for the perceptron algorithm. The result of this processing, in the form of a linear decision function, is given below as Equation (17), which defines a four-dimensional boundary plane.

$$D_i = (965)A_i + (2709)P_i - (98633.57)R_i - (7583.862)C_i - 536878 \quad (17)$$

Figure 23:
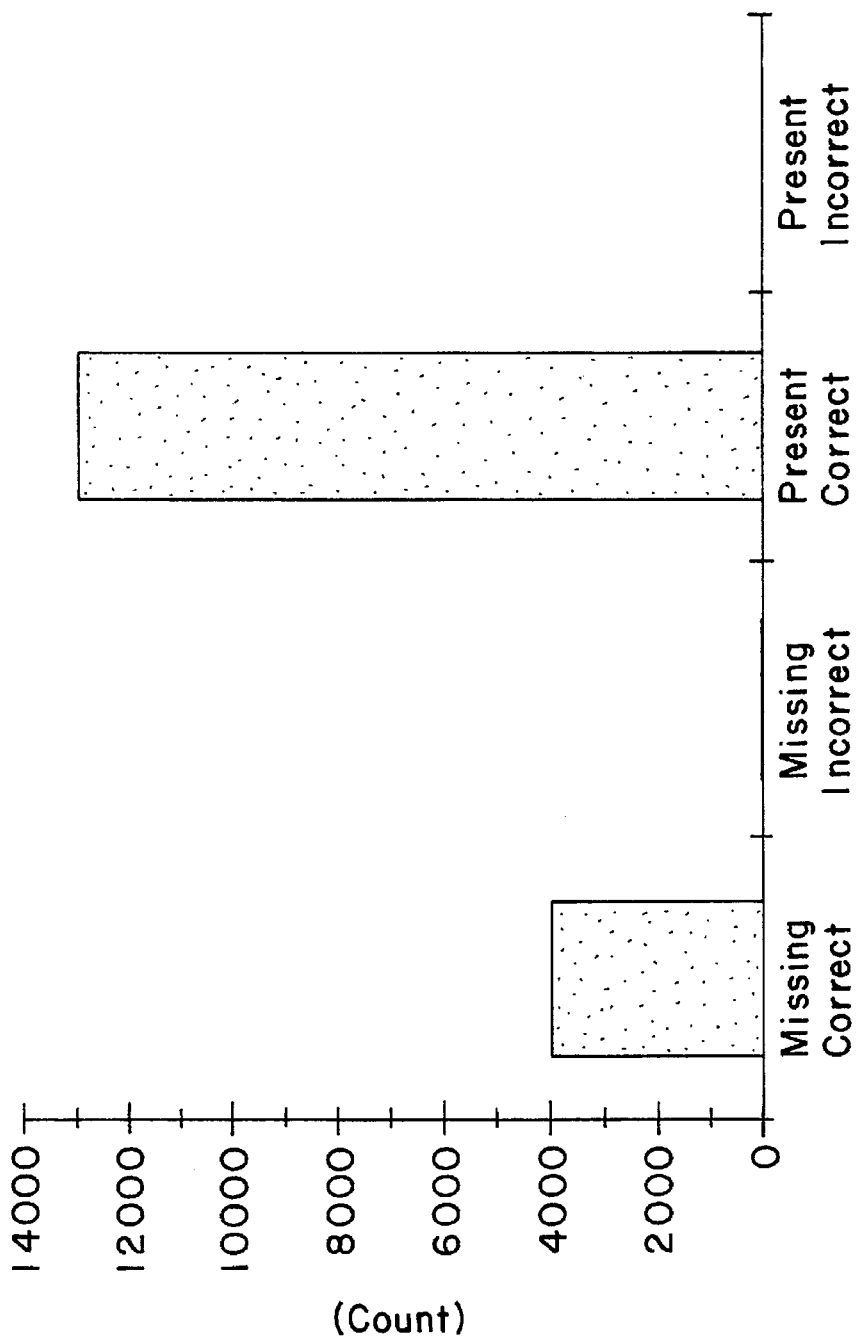
FIG. 23 shows a table and a bar graph illustrating the performance of a preferred embodiment of this invention.

Several processing boards were programmed with Equation (17) and then used to classify each object within the masks of over sixteen thousand package images. These tests are summarized in the table and bar graph of FIG. 23; and as shown therein, only about 0.22% of the packages were erroneously identified as missing lenses, and less than 0.1% of the packages were incorrectly identified as having lenses.

While it is apparent that the invention herein disclosed is well calculated to fulfill the objects previously stated, it will be appreciated that numerous modifications and embodiments may be devised by those skilled in the art, and it is intended that the appended claims cover all such modifications and embodiments as fall within the true spirit and scope of the present invention.

We claim:

1. A method for verifying the presence of a lens in a transparent package, comprising:

moving the package into an inspection position;

conducting a light beam through the package and onto an image plane to form an image of the package on the image plane; generating a set of signals representing the image on the image plane; and analyzing said set of signals to determine whether a lens is present in the package, said analyzing step including i) searching the package image for images of discrete objects, ii) for each object image found in the package image, identifying values for a plurality of parameters, and analyzing said identified values according to a predetermined procedure to identify the object as a lens or as not a lens including a) for each of said parameters,
      1) assigning a weight to the parameter, and
      2) multiplying the value identified for the parameter by the weight assigned to the parameter to determine a weighted value for the parameter;

b) summing the weighted values for the parameters to determine a sum; and c) comparing said sum to a preset value to identify the object as a lens or as not a lens, iii) generating a lens present signal if one object image found in the package image is identified as a lens, iv) generating a lens missing signal if no object images are found in the package image, or if all object images found in the package image are identified as not lenses.

2. A method according to claim 1, wherein:

the step of identifying values for a plurality of parameters includes the step of identifying values for at least four parameters;

the step of analyzing said identified values includes analyzing the identified values according to the equation:

$$D=\omega_a A+\omega_p P+\omega_r R+\omega_c C+\omega_5$$

where A, P, R, and C represent the values assigned to the four parameters, where $\omega_a$, $\omega_p$, $\omega_r$, and $\omega_c$ represent the weights assigned to the four parameters, and where $\omega_5$ is a predetermined constant; and identifying the object as a lens if D is less than or equal to zero, and identifying the object as not a lens if D is greater than zero.

3. A method according to claim 1, wherein each found object image has a perimeter, and wherein the step of identifying values for the plurality of parameters includes the step of determining the length of the perimeter of the object image.

4. A method according to claim 1, wherein each found object image has a width and a height, and wherein the step of identifying values for the plurality of parameters includes the steps of:

determining the width, a, and the height, b, of the object image; and determining a value, A, for one of the parameters according to the equation A=a·b.

5. A method according to claim 1, wherein each found object image has a width and a height, and wherein the step of identifying values for the plurality of parameters includes the steps of determining the width, a, and the height, b, of the object image; and determining a value, R, for one of the parameters according to the equation R=a/b.

6. A system for verifying the presence of a lens in a transparent package, comprising:

a transport subsystem for moving the package into an inspection position;

a detector comprising an array of pixels;

an illumination subsystem for generating a light beam and conducting the light beam through the package at the inspection position and onto the array of pixels to form an image of the package on said array of pixels;

a data value generator to assign to each of at least a group of the pixels a data value representing the intensity of the light beam on the pixel; and a processor to process said data values to determine whether a lens is present in the package, the processor including i) means to search the package image for images of discrete objects, ii) means to identify values for a plurality of parameters of each object image found, and to analyze the identified values for the parameters of each object image according to a predetermined procedure to identify the object as a lens or as not a lens, wherein the means to identify values for the parameters includes:

means to assign a weight to each parameter;

means to multiply the value assigned to each parameter by the weight assigned to the parameter to determine a weighted value for the parameter;

means to sum the weighted values for the parameters for each object image found to determine a sum for the object image; and means to compare the sum for each object image found to a preset value to identify the object as a lens or as not a lens, and iii) a signal generator to generate a lens present signal if one object image found in the package image is identified as a lens; and to generate a lens missing signal if no object images are found in the package, or if all object images found in the package image are identified as not lenses.

7. A system according to claim 6, wherein each found object image has a perimeter, and the means to identify values for the parameters further includes means to determine the length of the perimeter of each found object.

8. A system according to claim 6, wherein each found object image has a width, a, and a height, b, and the means to identify values for the parameters further includes means to determine the width and the height of each found object image, and to determine a value, A, for one of the parameters for each found object image according to the equation A=a·b.

* * * * *